United States Patent
Hammond et al.

(10) Patent No.: US 9,492,428 B2
(45) Date of Patent: Nov. 15, 2016

(54) COMPOUNDS, COMPOSITIONS, PHARMACEUTICAL COMPOSITIONS, AND METHODS OF USE

(71) Applicants: University of Louisville Research Foundation, Inc., Louisville, KY (US); Cayetano Heredia University, S.M.P. Lima (PE)

(72) Inventors: Gerald B. Hammond, Shelbyville, KY (US); Zhuang Jin, West Palm Beach, FL (US); Paula J. Bates, Louisville, KY (US); Elsa Merit Reyes-Reyes, Prospect, KY (US); Abraham Vaisberg, Lima (PE)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/358,731

(22) PCT Filed: Nov. 16, 2012

(86) PCT No.: PCT/US2012/065483
§ 371 (c)(1),
(2) Date: May 16, 2014

(87) PCT Pub. No.: WO2013/074905
PCT Pub. Date: May 23, 2013

(65) Prior Publication Data
US 2015/0025129 A1    Jan. 22, 2015

Related U.S. Application Data

(60) Provisional application No. 61/560,502, filed on Nov. 16, 2011, provisional application No. 61/593,135, filed on Jan. 31, 2012.

(51) Int. Cl.
*A61K 31/366* (2006.01)
*A61K 36/81* (2006.01)

(52) U.S. Cl.
CPC .............. *A61K 31/366* (2013.01); *A61K 36/81* (2013.01)

(58) Field of Classification Search
None
See application file for complete search history.

(56) References Cited

PUBLICATIONS

Simone, Oncology: Introduction, Cecil Textbook of Medicine, 20th Edition, 1996 vol. 1, pp. 1004-1010.*
International Search Report and Written Opinion from PCT/US2012/065483 mailed Jan. 24, 2013, 7 pages.
Aponte et al., "Anti-Infective and Cytotoxic Compounds Present in Blepharodon nitidum" Planta Medica (2008a) vol. 74, No. 4, pp. 407-410.
Aponte et al., "Isolation of Cytotoxic Metabolites from Targeted Peruvian Amazonian Medicinal Plants" J. Nat. Prod. (2008b) vol. 71, pp. 102-105.

(Continued)

*Primary Examiner* — San-Ming Hui
*Assistant Examiner* — Andrew Lee
(74) *Attorney, Agent, or Firm* — Calfee, Halter & Griswold LLP; Harry J. Guttman

(57) ABSTRACT

Certain embodiments of the invention include compositions comprising a compound of Formula (I), and salts, isomers, and derivatives thereof. Pharmaceutical compositions of some embodiments of the present invention comprise a compound of Formula (I), and salts, isomers, and derivatives thereof. Other embodiments of this invention include methods for treating disease (e.g., cancer) and methods for administering a compound of Formula (I), and salts, isomers, and derivatives thereof.

26 Claims, 20 Drawing Sheets

(56) References Cited

PUBLICATIONS

Aponte et al., "A Multipronged Approach to the Study of Peruvian Ethnomedicinal Plants: A Legacy of the ICBG-Peru Project" J. Nat. Prod. (2009) vol. 72, No. 3, pp. 524-526.
Aponte et al., "Cytotoxic and Anti-infective Sesquiterpenes Present in Plagiochila disticha (Plagiochilaceae) and Ambrosia peruviana (Asteraceae)" Planta Medica (2010) vol. 76, No. 7, pp. 705-707.
Aponte et al., "Cytotoxic and Anti-infective Phenolic Compounds Isolated from Mikania decora and Cremastosperma microcarpum" Planta Medica (2011) vol. 77, pp. 1597-1599.
Bastos et al., "Antinociceptive effect of the aqueous extract obtained from roots of Physalis angulata L. on mice" J. Ethnopharmacol. (2006) vol. 103, pp. 241-245.
Bastos et al., "Physalis angulata extract exerts anti-inflammatory effects in rats by inhibiting different pathways" J. Ethnopharmacol. (2008) vol. 118, pp. 246-251.
Bates et al. Chapter 21: "G-Rich Oligonucleotides for Cancer Treatment" at pp. 379-392 in Methods in Molecular Biology, Gene Therapy of Cancer, vol. 542, Editors Walther et al. (2009) Humana Press, New York, New York USA.
Brustolim et al., "Activity of Physalin F in a Collagen-Induced Arthritis Model" J. Nat. Prod. (2010) vol. 73, pp. 1323-1326.
Caceres et al., "Antiogonorrhoeal Activity of Plants Used in Guatemala for the Treatment of Sexually Transmitted Diseases" J. Ethnopharmacol. (1995) vol. 48, pp. 85-88.
Castro et al., "Immune depression in Rhodnius prolixus by seco-steroids, physalins" Journal of Insect Physiology (2008) vol. 54, pp. 555-562.
Chen et al., "Natural withanolides: an overview" Natural Product Reports (2011) vol. 28, pp. 705-740.
Chiang et al., "Inhibitory effects of physalin B and physalin F on various human Leukemia cells in vitro" Anticancer Research (1992) vol. 12, pp. 1155-1162.
Dos Santos et al., "Molluscicidal Activity of Physalis angulata L. Extracts and Fractions on Biomphalaria tenagophila (d'Orbigny, 1835) under Laboratory Conditions" Mem. Inst. Oswaldo Cruz., Rio de Janeiro (2003) vol. 98, No. 3, pp. 425-428.
Glotter, "Withanolides and related ergostane-type steroids" Nat. Prod. Rep. (1991) vol. 8, pp. 415-440.
Hseu et al., "Inhibitory effects of Physalis angulata on tumor metastasis and angiogenesis" J. Ethnopharmacol. (2011) vol. 135, pp. 762-771.
Hsieh et al., "Physalis angulata induced G2/M phase arrest in human breast cancer cells" Food and Chemical Toxicology (2006) vol. 44, pp. 974-983.
Januario et al., "Antimycobacterial physalins from Physalis angulata L. (Solanaceae)" Phytother. Res. (2002) vol. 16, pp. 445-448.
Jin et al., "Physangulidines A, B and C: three new antiproliferative withanolides from Physalia angulata L." Org. Lett. (2012) vol. 14, No. 5, pp. 1230-1233.
Kuo et al., "Physanolide A, a novel skeleton steroid, and other cytotoxic principles from Physalis angulata" Org. Lett. (2006) vol. 8, No. 14, pp. 2953-2956.
Lan et al., "New cytotoxic withanolides from Physalis peruviana" Food Chemistry (2009) vol. 116, pp. 462-469.
Lee et al', "Induction of heat-shock response and alterations of protein phosphorylation by a novel topoisomerase II inhibitor, withangulatin A, in 9L rat brain tumor cells" J Cell Physiol. (1991) vol. 149, No. 1, pp. 66-76.
Lee et al., "Oxidative stress involvement in Physalis angulata-induced apoptosis in human oral cancer cells" Food Chem Toxicol (2009) vol. 47, pp. 561-570.
Luis et al., "Withajardins, withanolides with a new type of skeleton structure of withajardins A, B, C and D absolute configuration of withajardin C" Tetrahedron (1994) vol. 50, No. 4, pp. 1217-1226.
Magalhães et al., "In-vitro and In-vivo antitumour activity of physalins B and D from physalis angulata" J Pharma Pharmacol. (2006) vol. 58, pp. 235-241.
Martinez, "Revision of Physalis Section Epeteiorhiza (Solanaceae)" Anales del Instituto de Biologia Universidad Nacional Autonoma de Mexico, Serie Botanica (1998) vol. 69, No. 2, pp. 71-117.
Misico et al., "Withanolides and Related Steroids" at pp. 127-229 in Progress in the Chemistry of Organic Natural Products, vol. 94, Editors Kinghorn et al. (2011) Springer-Verlag/Wien, New York, New York USA.
Osho et al., "Antimicrobial Activity of Essential Oils of Physalis Angulata. L" African Journal of Traditional, Complement and Altern Med. (2010) vol. 7, No. 4, pp. 303-306.
Park et al., "Detergent and enzyme treatment of apoptotic cells for the observation of DNA fragmentation" BioTechniques (1998) vol. 24, No. 4, pp. 558-560.
Pinto et al., "Topical anti-inflammatory potential of Physalin E from Physalis angulata on experimental dermatitis in mice" Phytomedicine (2010) vol. 17, pp. 740-743.
Ramallo et al., "Chemically Engineered Extracts: Source of Bioactive Compounds" Accounts of Chemical Research (2011) vol. 44, No. 4, pp. 241-250.
Reyes-Reyes et al., "Physangulidine A, a Withanolide from Physalis angulata, Perturbs the Cell Cycle and Induces Cell Death by Apoptosis in Prostate Cancer Cells" J. Nat. Prod. (2013) vol. 76, pp. 2-7.
Sá et al., "Antimalarial activity of physalins B, D, F, and G" J. Nat Prod. (2011) vol. 74, pp. 2269-2272.
Soares et al., "Inhibition of macrophage activation and lipopolysaccaride-induced death by seco-steroids purified from Physalis angulate L." Eur. J. Pharmacol (2003) vol. 459, pp. 107-112.
Ulukaya et al., "Apoptosis: why and how does it occur in biology?" Cell Biochem. Funct. (2011) vol. 29, pp. 468-480.
Wu et al., "Antihepatoma activity of Physalis angulata and P. peruviana extracts and their effects on apoptosis in human Hep G2 cells" Life Sci. (2004) vol. 74, pp. 2061-2073.
Boyd et al., "Some Practical Considerations and Applications of the National Cancer Institute In Vitro Anticancer Drug Discovery Screen" Drug Development Research (1995) vol. 34, pp. 91-109.
Choi et al., "Cancer-selective antiproliferative activity is a general property of some G-rich oligodeoxynucleotides" Nucleic Acids Research (2010) vol. 38, No. 5, pp. 1623-1635.
Damu et al., "Isolation, Structures, and Structure-Cytotoxic Activity Relationships of Withanolides and Physalins from Physalis angulata" J. Nat. Prod. (2007) vol. 70, pp. 1146-1152.
Skehan et al., "New Colorimetric Cytotoxicity Assay for Anticancer-Drug Screening" Articles (1990) vol. 82, No. 13, pp. 1107-1112.

* cited by examiner

|       | GI$_{50}$ μM |
|-------|--------------|
| DU145 | 7.0          |
| PC3   | 5.0          |

FIG. 10A
24 h
FIG. 10B
48 h
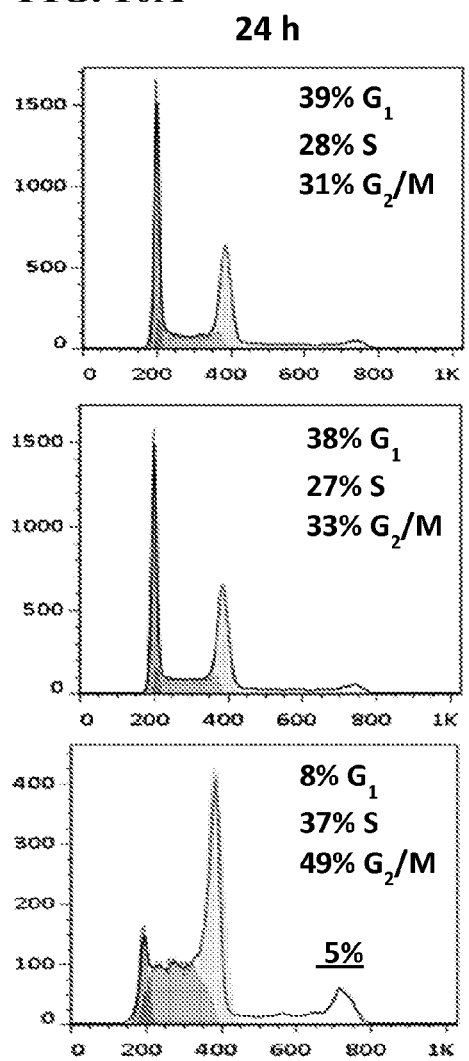
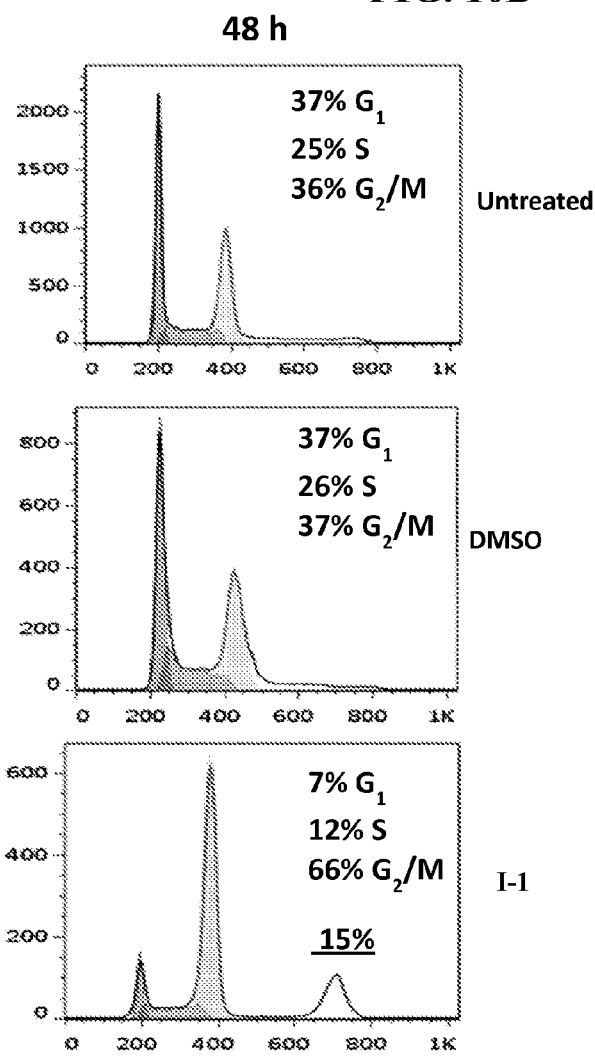

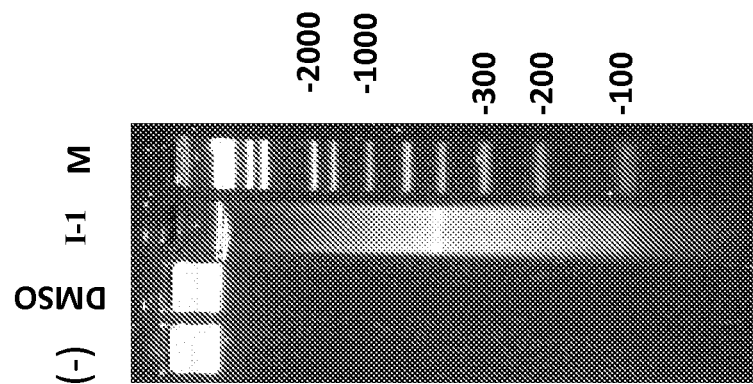
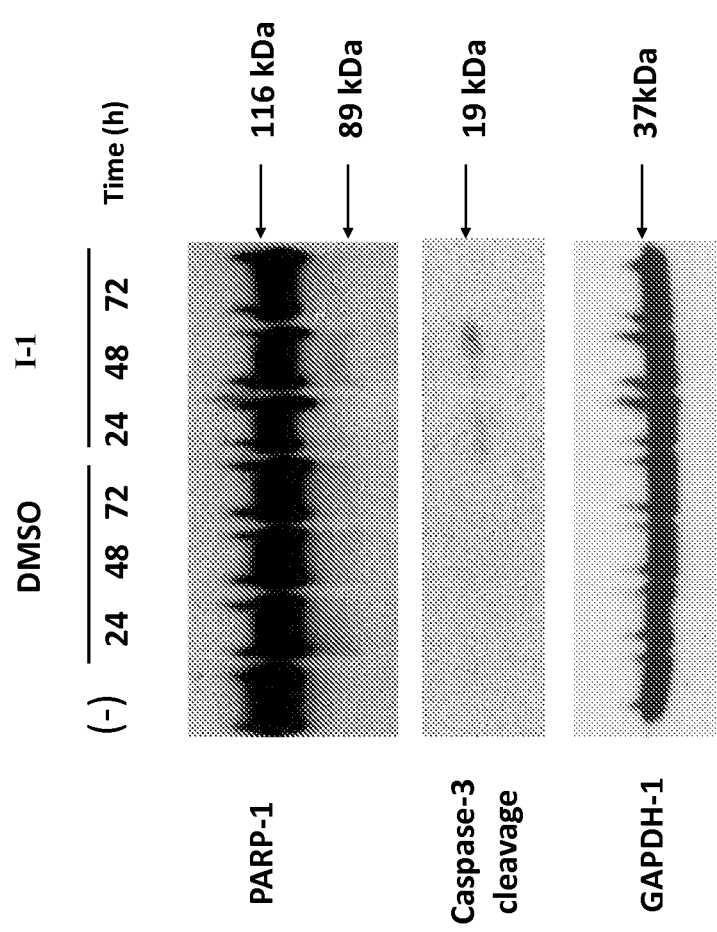
FIG. 11C
FIG. 11B

COMPOUNDS, COMPOSITIONS, PHARMACEUTICAL COMPOSITIONS, AND METHODS OF USE

CROSS-REFERENCE TO RELATED APPLICATIONS

This application is a National Stage Entry of International Application No. PCT/US2012/065483 filed Nov. 16, 2012, entitled "COMPOUNDS, COMPOSITIONS, PHARMACEUTICAL COMPOSITIONS, AND METHODS OF USE" which is herein incorporated by reference in its entirety, and which claims the benefit of U.S. Provisional Application No. 61/560,502, filed Nov. 16, 2011, entitled "COMPOUNDS WITH ANTI-DISEASE PROPERTIES" which is herein incorporated by reference in its entirety. This application also claims the benefit of U.S. Provisional Application No. 61/593,135, filed Jan. 31, 2012, entitled "COMPOUNDS AND THEIR USES TO TREAT DISEASES" which is herein incorporated by reference in its entirety.

GOVERNMENT RIGHTS

This invention was made with the following U.S. Government support: (a) grant number W81XWH-07-1-0299 awarded by U.S. Department of Defense Prostrate Cancer Research Program (PCRP) of the Office of the Congressionally Directed Medical Research Medical Research Program (CDMRP), (b) grant number W81XWH awarded by the Department of Defense from the Telemedicine and Advanced Technology Research Center of the US Army, (c) grant number DEFG02-08CH11538 awarded by the Department of Energy, and (d) grant number EPS-0447479 funded by NSF/EPSCoR to the Center for Regulatory and Environmental Analytical Metabolomics (CREAM) Mass Spectrometry Facility (University of Louisville). The Government has certain rights in this invention.

BACKGROUND

Some cancer treating molecules are isolates of or synthesized from extracts of plants. Disclosed herein are molecules, some of which come from plants that can be used to treat cancer.

SUMMARY

Some embodiments of the invention include a composition comprising a compound, where the compound is selected from Formula (I), salts of Formula (I), isomers of Formula (I), and derivatives (e.g., esters, ethers, or amides) of Formula (I), and the concentration of the compound is at least about 0.20% by weight. In another embodiment, the concentration of the compound can be at least about 10.0% by weight, at least about 50.0% by weight, or at least about 90.0% by weight. In some embodiments $R^1$, $R^2$, and $R^3$ can be the same or different and are selected from H, hydroxyl, halogen, methyl, ethyl, methoxy, and ethoxy. In still other embodiments, the compound can be selected from I-1, I-2, and I-3. In some instances, the compound in the composition induces apoptosis or causes arrest in the $G_2/M$ phase of the cell cycle.

In some embodiments of the invention, a pharmaceutical composition comprises a compound and the compound is selected from Formula (I), salts of Formula (I), isomers of Formula (I), and derivatives (e.g., esters, ethers, or amides) of Formula (I). In other embodiments, the concentration of the compound can be at least about 0.2% by weight or at least about 10.0% by weight. In certain embodiments, $R^1$, $R^2$, and $R^3$ of the compound can be the same or different and are selected from H, hydroxyl, halogen, methyl, ethyl, methoxy, and ethoxy. In other embodiments, the compound is selected from I-1, I-2, and I-3. The compound in the composition can sometimes induce apoptosis or causes arrest in the $G_2/M$ phase of the cell cycle. In some instances, the compound is present in a therapeutically effective amount to treat a disease, such as cancer. The composition can further comprise a formulary ingredient and/or pyrogen-free water.

Other embodiments of the invention include a method for treating a disease in an animal comprising administering a composition comprising a compound, to the animal, where the compound is selected from Formula (I), salts of Formula (I), isomers of Formula (I), and derivatives (e.g., esters, ethers, or amides) of Formula (I). The method can further comprise identifying an animal with the disease. In some embodiments, the disease to be treated is a cancer, a cancerous tumor, basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, or leukemias. In still other embodiments, the animal is a mammal, such as a human. In some instances, the administering is by an oral route or by a parenteral route. In other embodiments, the compound is selected from I-1, I-2, and I-3.

Some embodiments of the invention include a method for administering the composition comprising a compound to a cell, where the compound is selected from Formula (I), salts of Formula (I), isomers of Formula (I), and derivatives (e.g., esters, ethers, or amides) of Formula (I). In some instances, the administration is to an animal, such as a human or a mammal Sometimes the administering is by an oral route or by a parenteral route. In certain embodiments, the concentration of the compound is at least about 0.2% by weight or at least about 10% by weight. In still other embodiments, the compound is selected from I-1, I-2, and I-3. In some embodiments, the cell is a mammalian cell, a human cell, part of an organ, or is from a multicellular organism. Sometimes, the cell can be DU145 cells, PC-3 cells, RWPE-1 cells, LNCaP, Lewis lung carcinoma cells, B16F10 melanoma cells, TC-1 cervical carcinoma cells, HS27 cells, MCF7 cells, MDA-MB-231 cells, A549 cells, THP-1 cells, 300.19 cells, Hela cells, A375 cells, SK-MEL-28 cells, GM0637 cells, tGM24 cells, CHO cells, mouse cells, or African green monkey cells. In other embodiments, the cell is a transfected cell.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 10. Flow cytometric analysis of cell cycle parameters. DU145 prostate cancer cells were incubated for 24 h (A) or for 48 h (B) in the presence of 10 μM compound I-1 or vehicle (DMSO), or without additive (untreated). Cells were then harvested by trypsinization, fixed, and stained with propidium iodide for analysis by flow cytometry. Each histogram indicates the percent of cells in $G_1$, S, and $G_2$/M phases of the cell cycle. Data were gated to exclude apoptotic cells for these calculations. A small population of aneuploid cells with >4n DNA content, which became apparent in the cells treated with compound I-1, is also indicated (percentage underlined).

DETAILED DESCRIPTION

Figure 1:
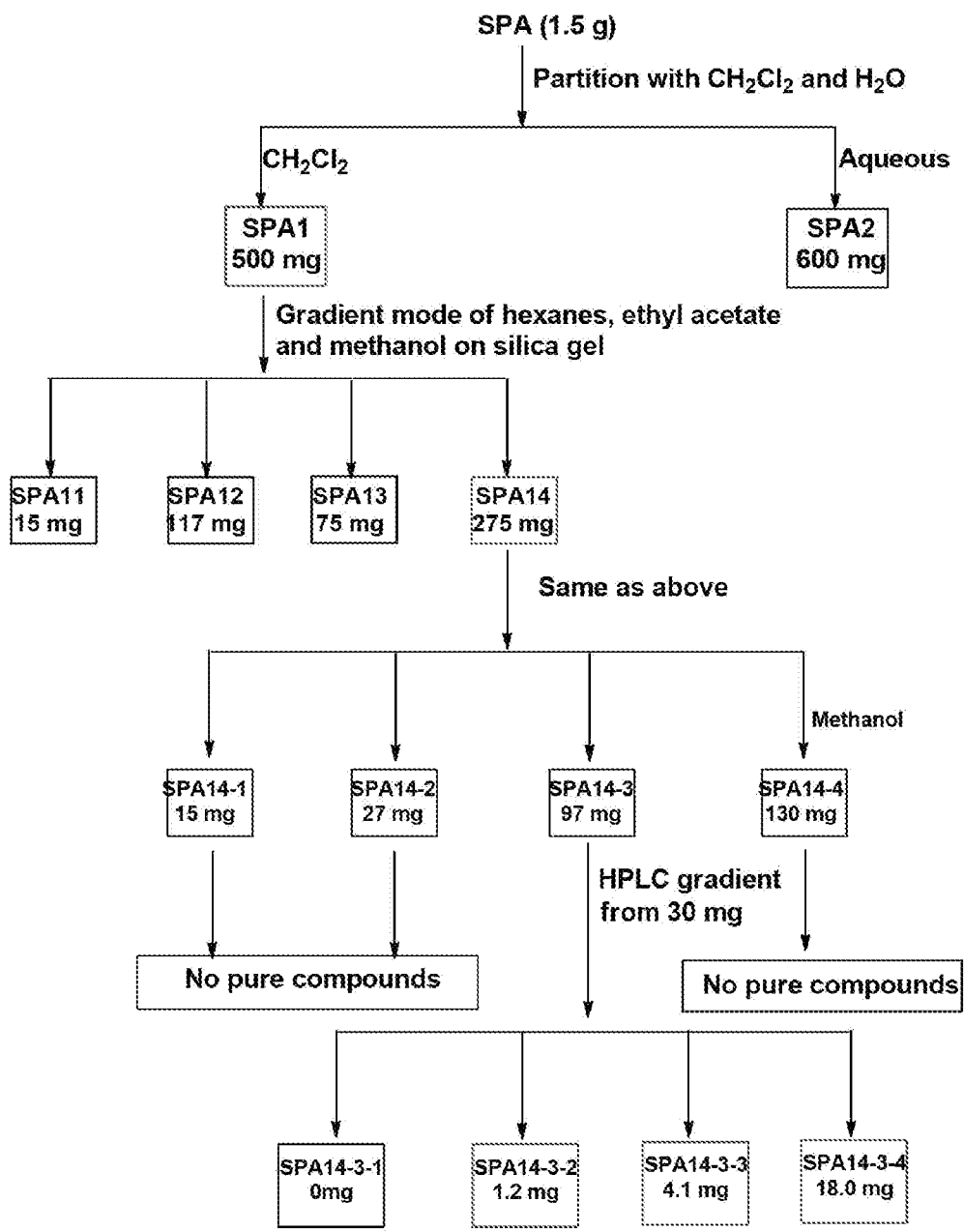
FIG. 1. Scheme for isolation of some compounds from *Physalis angulate* L. SPA14-3-2 is pure compound I-2. SPA14-3-3 is pure compound I-3. SPA14-3-4 is pure compound I-1.

Some embodiments of the invention include compounds of Formula (I).

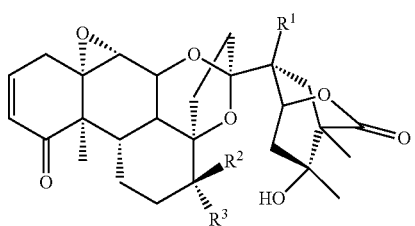

(I)

$R^1$, $R^2$, and $R^3$ can be the same or different, and can be H, halogen (e.g., F, Cl, Br, or I), hydroxyl, methoxy, ethoxy, propoxy, butoxy, pentoxy, hexoxy, methyl, ethyl, propyl, butyl, pentyl, hexyl, or heptyl.

Some embodiments of Formula I include the following compounds:

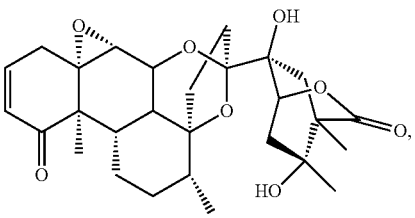

I-1

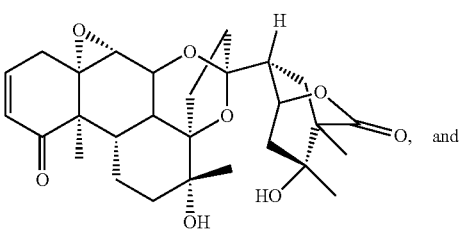

I-2

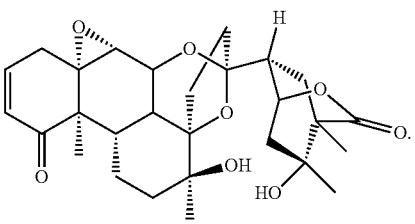

I-3

The compounds of the invention (e.g., any of the compounds of Formula (I)) can be in the form of salts, optical and geometric isomers, and salts of isomers. Also, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. For acidic compounds, salts can include metals, amines, or organic cations (e.g. quaternary ammonium). Furthermore, simple derivatives of the compounds (e.g., ethers, esters, or amides) which have desirable retention and release characteristics but which are easily hydrolyzed by body pH, enzymes, or other suitable means, can be employed.

Some compounds of the invention can, but are not required to, modulate one or more of the following (1) mitotic progression, (2) capcase-3 activity, (3) cleavage of PARP-1, (4) $G_2$ to M phase transition, (5) arrest in the $G_2$/M phase of the cell cycle (6) mitotic arrest, (7) programmed cell death (e.g., apoptosis), (8) mitotic catastrophe, (9) pause in mitosis, (10) disruption of cell cycle regulation, (11) DNA replication, or (12) cell division.

Some embodiments of the invention include administration of at least one compound of the invention to a cell. The cell can be a unicellular organism, or can be obtained from a multicellular organism, e.g., isolated cells from a multicellular host. The cell can be one of many cells treated. The cell can be a eukaryotic cell which can include but is not limited to fungi, yeast, insect cells (e.g., Spodoptera frugiperda (SF9)), animal cells such as CHO and mouse cells (e.g., Lewis lung carcinoma cells, B16F10 melanoma cells, and TC-1 cervical carcinoma cells), African green monkey cells (such as COS 1, COS 7, BSC 1, BSC 40, and BMT 10), and human cells (e.g., human carcinoma cells, DU145 cells, PC-3 cells, RWPE-1 cells, LNCaP, A375 cells, HeLa cells, SK-MEL-28 cells, tGM24 cells, GM0637 cells, HS27 cells, MCF7 cells, MDA-MB-231 cells, A549 cells, THP-1 cells, and 300.19 cells), as well as plant cells. Of course, the cell may be transfected with one or more genes.

The compounds of the invention can be administered to animals by any number of administration routes or formulations. The compounds of the invention can also be used to treat animals for a variety of diseases. Animals include but are not limited to canine, bovine, porcine, avian, mammalian, and human.

Diseases that can be treated using the compounds of the invention include, but are not limited to cancers (such as cancerous tumors). Cancers that can be treated include, but are not limited to, basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, the lymph node, bone marrow, liver tissues, uterine cancer, and leukemias.

The route of administration of the compounds of the invention may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route. and the ocular route. The choice of administration route can depend on the compound identity, such as the physical and chemical properties of the compound, as well as the age and weight of the animal, the particular disease, and the severity of the disease. Of course, combinations of administration routes can be administered, as desired.

One or more compounds of the invention can be part of a composition and can be in an amount (by weight of the total composition) of at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%.

One or more compounds of the invention can be part of a composition and can be in an amount of about 0.5 µM, about 1.0 µM, about 2.0 µM, about 5.0 µM, about 10.0 µM, about 20.0 µM, about 25.0 µM, about 30.0 µM, about 40.0 µM, about 50.0 µM, about 60.0 µM, about 70.0 µM, about 75.0 µM, about 80.0 µM, about 90.0 µM, about 100.0 µM, about 150.0 µM, about 200.0 µM, at least about 0.1 µM, at least about 1.0 µM, at least about 10.0 µM, at least about 25.0 µM, at least about 50.0 µM, no more than about 75.0 µM, no more than about 100.0 µM, no more than about 200.0 µM, no more than about 400.0 µM, from about 0.5 µM to about 400.0 µM, from about 1.0 µM to about 100.0 µM, or from about 2.0 µM to about 50.0 µM.

A composition comprising a compound of the invention can include, but is not limited to, a single stereoisomer of the compound, a racemic mixture of the compound, or a scalemic mixture of the compound.

When a composition comprises a compound with at least two chiral centers, it is to be understood that the composition can be, but is not limited to, a composition comprising a diastereomer free of other diastereomers, a composition comprising a pair of diastereomers free from other diastereomeric pairs, a composition comprising mixtures of diastereomers, mixtures of diastereomeric pairs, a composition comprising mixtures of diastereomers in which one diastereomer is enriched relative to the other diastereomer(s), or a composition comprising mixtures of diastereomeric pairs in which one diastereomeric pair is enriched relative to the other diastereomeric pair(s).

One or more compounds of the invention can be purified or isolated in an amount (by weight of the total composition) of at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 1% to about 95%, from about 10% to about 90%, or from about 25% to about 75%.

In some embodiments, one or more compounds of the invention can be used as part of a pharmaceutical composition. "Pharmaceutical composition" means a composition suitable for use in the treatment of animals. In some instances, the pharmaceutical composition is non-toxic and does not cause additional side effects compared to the drug delivered. In some therapies which are toxic (e.g., some cancer therapies), a pharmaceutical composition can deliver an amount of drug (e.g., one or more of compounds from Formula (I)) sufficient to kill or alter the diseased cells (e.g., cancer cells or tumor cells) and not kill (or alter to a lesser extent) the non-diseased cells; there may be side effects inherent to the drug (e.g., the drug may harm the patient or the drug may be toxic or harmful to some non-diseased cells in the patient).

"Therapeutically effective amount" means an amount effective to achieve a desired and/or beneficial effect. An effective amount can be administered in one or more administrations. For some purposes of this invention, a therapeutically effective amount is an amount appropriate to treat an indication such as cancer. By treating an indication is meant achieving any desirable effect, such as one or more of palliate, ameliorate, stabilize, reverse, slow, or delay disease progression, increase the quality of life, or to prolong life. Such achievement can be measured by any method known in the art, such as physical measurement of mitotic arrest, mitotic catastrophe, cell phenotype, monitoring of the level of cancerous antigens in blood serum, or measuring patient life.

In some embodiments, one or more compounds of the invention can be part of a pharmaceutical composition and can be in an amount of at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 1% to about 95%, from about 10% to about 90%, or from about 25% to about 75%. The pharmaceutical composition can be presented in a dosage form which is suitable for the topical, subcutaneous, intrathecal, intraperitoneal, oral, parenteral, rectal, cutaneous, nasal, vaginal, or ocular administration route. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active compound substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of treating an organism, which can involve treatment with an amount of the compound of the invention that is effective to treat the disease, condition, or disorder that the organism has, or is suspected of having, or to bring about a desired physiological effect. In some embodiments, the amount of one of at least one compound of the invention is administered to mammals (e.g., humans) at a concentration of about 0.05 to about 15 mg/kg body weight, about 0.2 to about 10 mg/kg body weight, about 0.5 to about 7 mg/kg body weight, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 6.5 mg/kg human body weight. In some instances, a mouse can be administered a dosage of about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention can be administered in combination with one or more other therapeutic agents for a given disease, condition, or disorder.

EXAMPLE SET 1

Figure 2A:
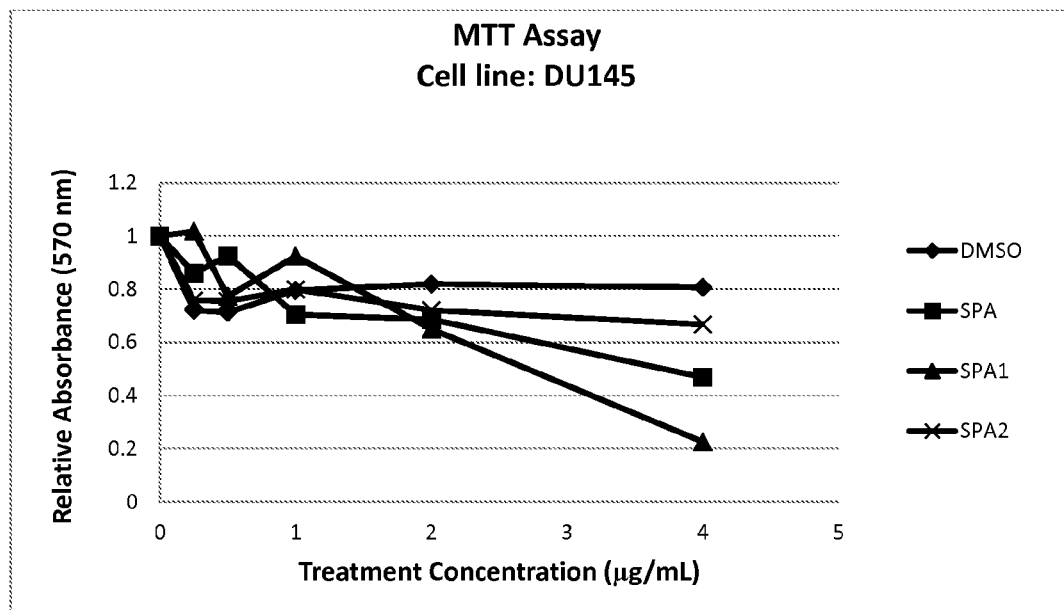
FIG. 2. Bioassay of SPA, SPA1, and SPA2. MTT assays using SPA, SPA1, and SPA2 fractions against DU145, LNCaP, and RWPE-1 cells lines.
Figure 2B:
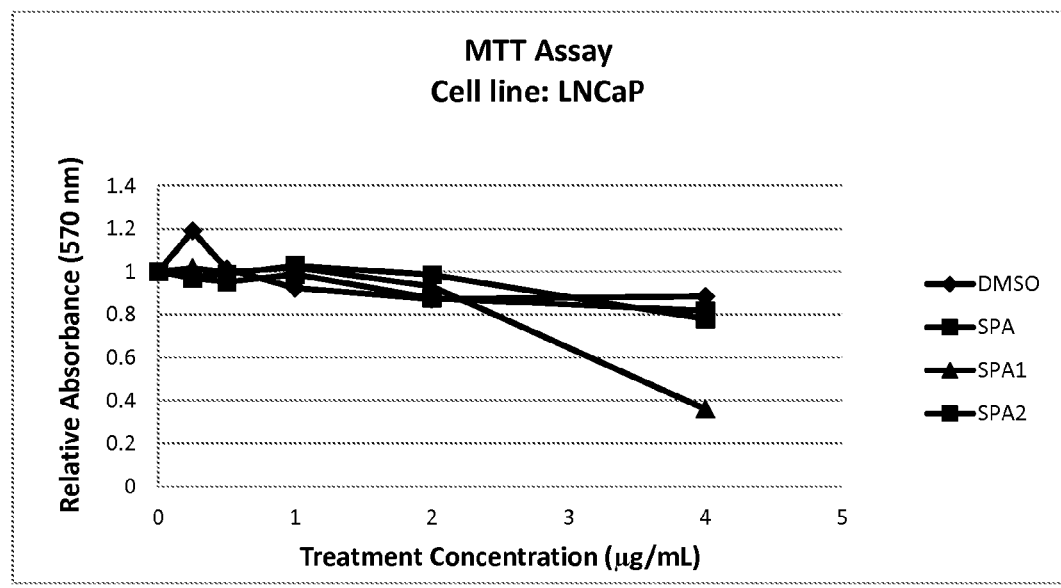
Figure 2C:
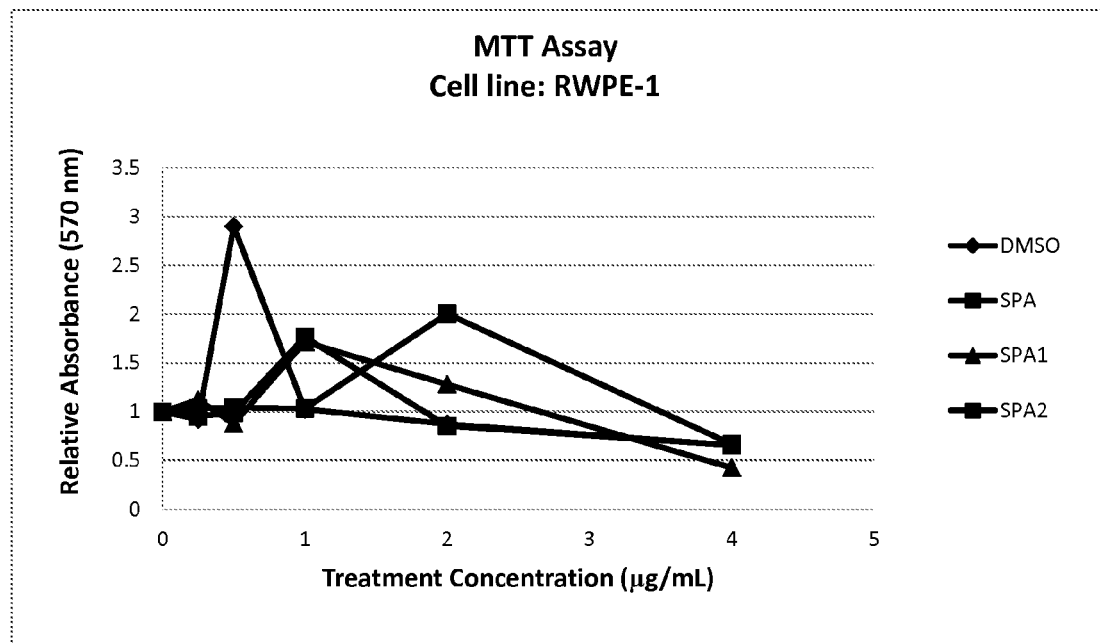
Figure 3A:
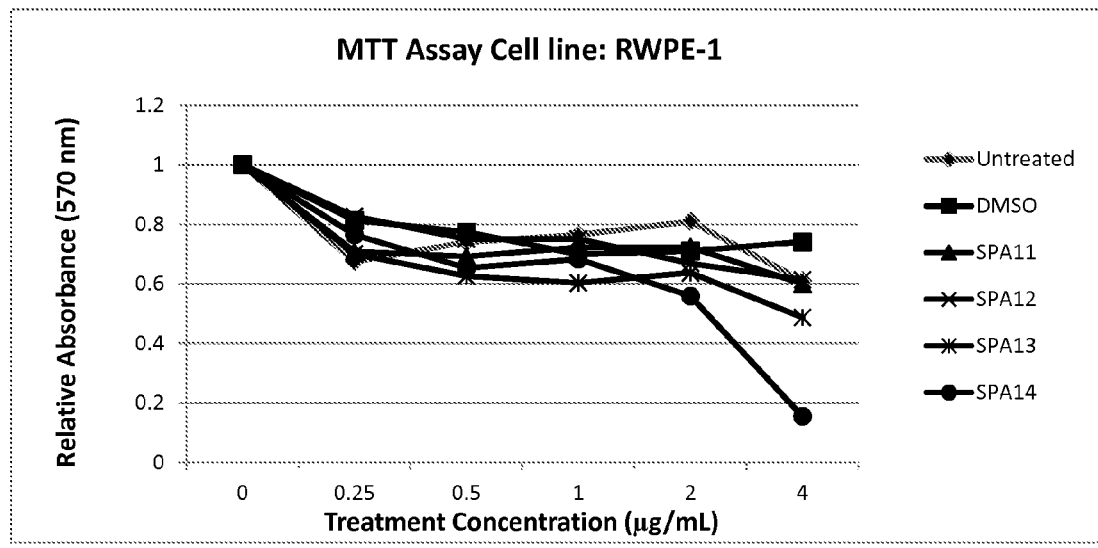
FIG. 3. Bioassay of SPA11, SPA12, and SPA13, and SPA 14. MTT assays using SPA11, SPA12, SPA13, and SPA14 fractions against DU145, LNCaP, RWPE-1, and PC-3 cells lines.
Figure 3B:
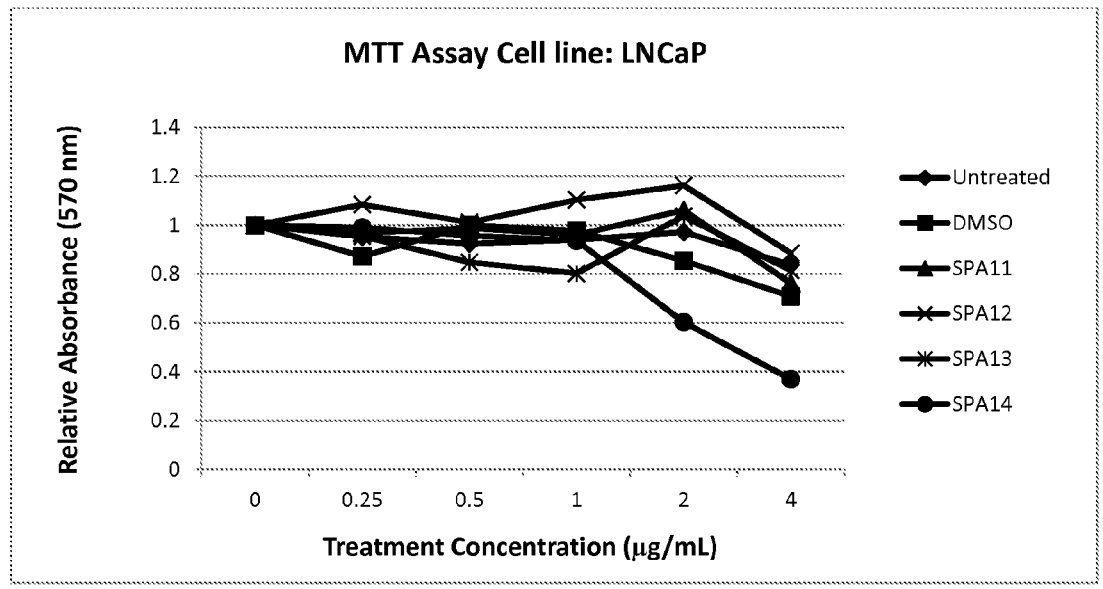
Figure 3C:
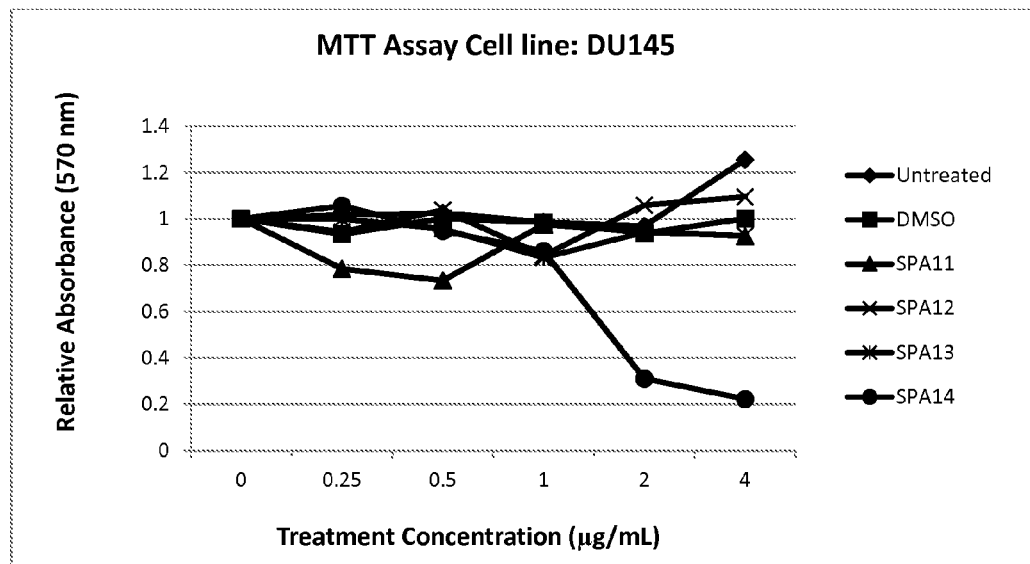
Figure 3D:
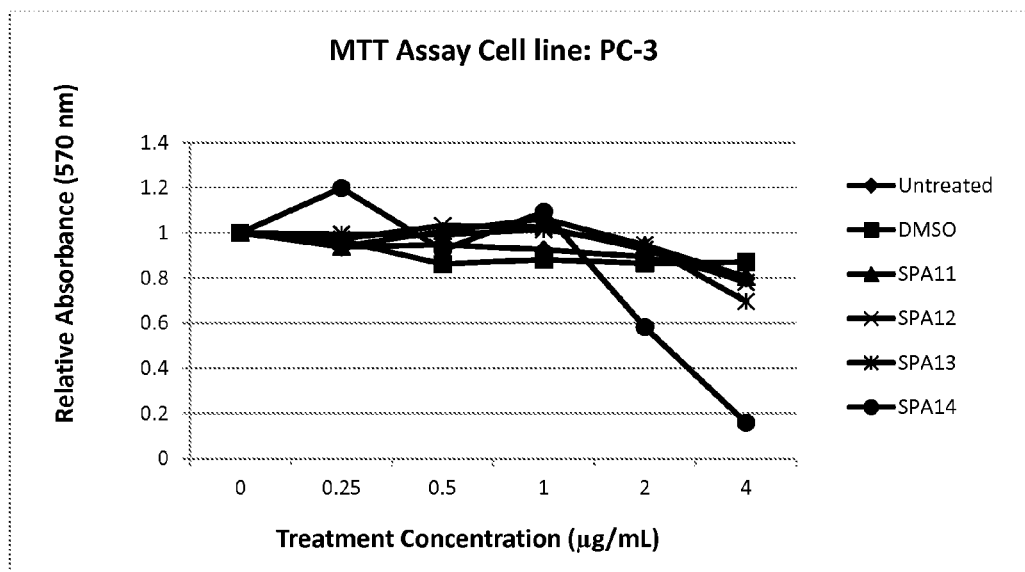
Figure 4A:
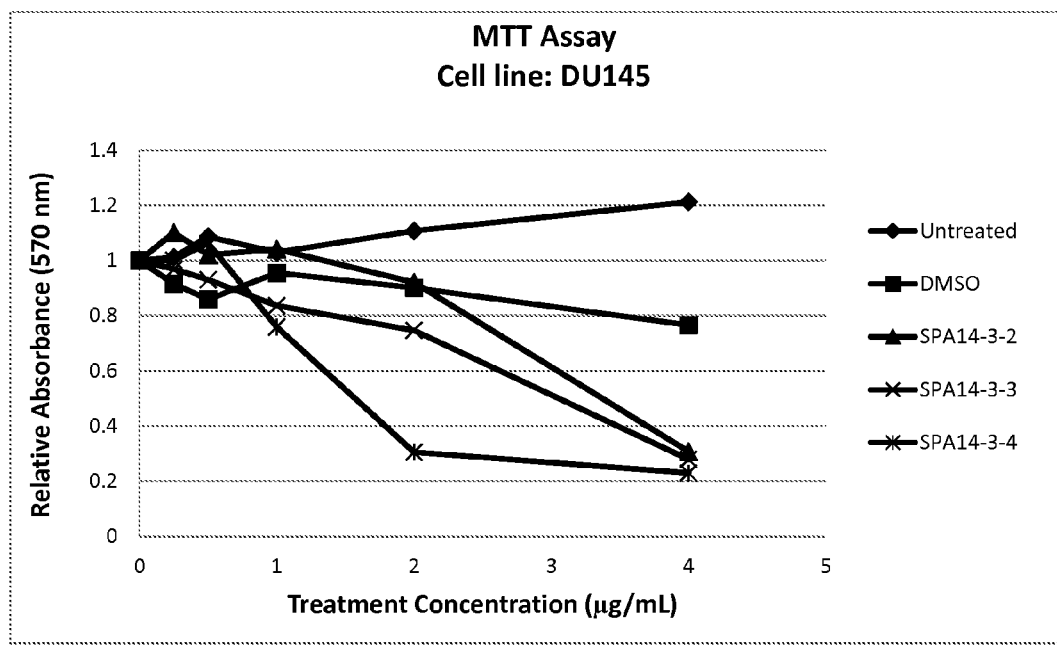
FIG. 4. Bioassay of compound I-1, compound I-2, and compound I-3. SPA14-3-2 is pure compound I-2. SPA14-3-3 is pure compound I-3. SPA14-3-4 is pure compound I-1. MTT assays using compound I-1, compound I-2, and compound I-3 against DU145 and RWPE-1 cells lines.
Figure 4B:
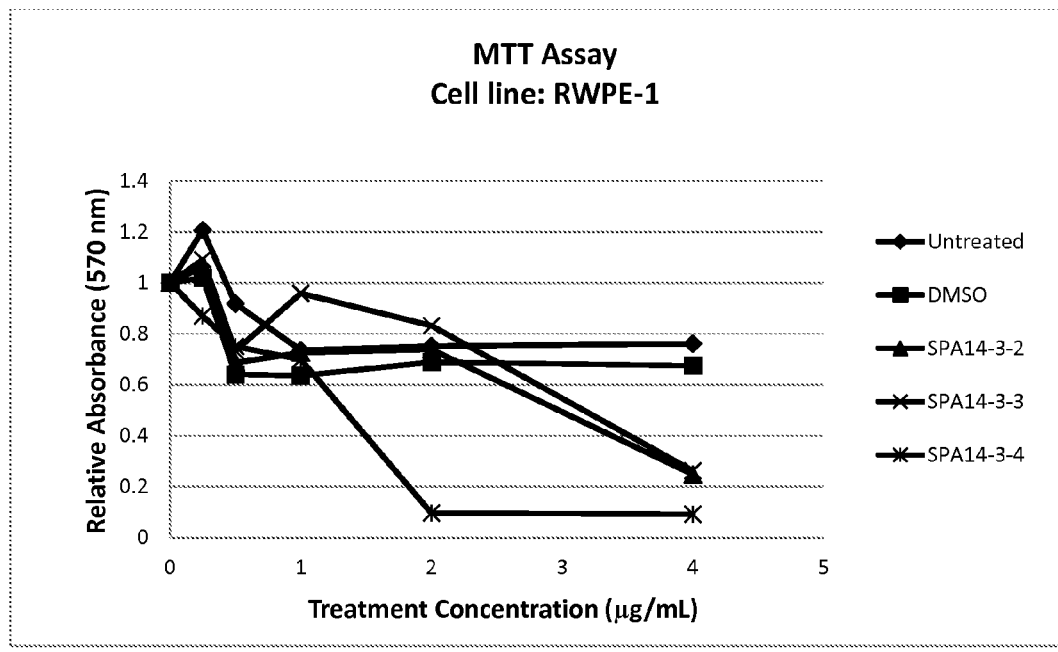

Isolation, NMR, and X-ray crystallographic analyses. Leaves, stems, and few fruits of *Physalis angulate* L (Solanaceae) were collected in Rio Domingusa. Kuith/Barranquita, Amazonas Department, Northeastern Peru, and identified by the team led by Walter Lewis (collection voucher 18597, Ext. 1159). The general scheme for isolating some compounds from *Physalis angulate* L is shown in FIG. 1. Dried and grounded material (46 g) was extracted with ethanol (1 L, 95%) for 7 days. The evaporated crude extract (6.26 g) was denoted SPA. An aliquot (1.5 g) of SPA was partitioned between dichloromethane (40 mL) and water (40 mL), affording two fractions: organic (SPA1, 500 mg) and aqueous (SPA2, 600 mg). All MTT assays were performed as described in Bates et al. "G-Rich Oligonucleotides for Cancer Treatment" Chapter 21 of Methods in Molecular Biology, Gene Therapy of Cancer, Wolfgang Walther and Ulrike S. Stein (eds.), Vol. 542, 2009, Humana Press. MTT assays showed that organic fraction (SPA1) was active (FIG. 2); therefore, this fraction was further treated on silica gel chromatography and eluted by hexane, ethyl acetate, and methanol in gradient mode to give four new fractions, SPA11 (15 mg), SPA12 (117 mg), SPA13 (75 mg), and SPA14 (275 mg), respectively. The most active fraction, SPA14 (FIG. 3), was further treated on silica gel chromatography and eluted by hexane, ethyl acetate, and methanol in gradient mode to provide four new fractions SPA14-1 (15 mg), SPA14-2 (27 mg), SPA14-3 (97 mg), and SPA14-4 (130 mg), respectively. SPA14-3 (30 mg) was treated on an HPLC using a reverse phase C18 column eluted in gradient mode of methanol and water (from 80% methanol to 100% methanol) and detected at 254 nm, yielding SPA14-3-1 (0 mg), SPA14-3-2 (1.2 mg of pure compound I-2), SPA14-3-3 (4.1 mg of pure compound I-3), and SPA14-3-4 (18 mg of pure compound I-1). All three showed cytotoxic activity against DU145 and RWPE-1 cell lines (FIG. 4).

Tables 1-3 show the detailed results of the NMR experiments used to help identify the structures of compounds I-1, I-2, and I-3. All NMR data were collected at 25.0° C. in $CDC_3$ at 699.81 MHz in a 5 mm $^1H\{^{13}C/^{15}N\}(^{13}C$ enhanced) Cold Probe on a VNMRS700 Varian (Agilent) Spectrometer.

TABLE 1

NMR data for compound I-1

| Position | $^{13}C$ NMR | HSQC | COSY | ROESY | HMBC |
|---|---|---|---|---|---|
| 1 | 201.825 | | | | 3, 4eq, 9, 19 |
| 2 | 129.261 | 6.08 (dd, J = 9.8, 2.8 Hz, 1H) | 3, 4ax | 3 | 4 |
| 3 | 143.748 | 6.86 (ddd, J = 9.8, 6.3, 2.8 Hz, 1H) | 2, 4eq | 2 | 4 |
| 4 | 32.064 | 2.95 (ax, dt, J = 18.2, 2.8 Hz, 1H) 1.93 (eq, dd, J = 18.2, 6.3 Hz, 1H) | Hax: 2 Heq: 3 | Hax: 19 Heq: 6 | 2, 3, 6, 7 |
| 5 | 62.596 | | | | 3, 4, 19 |
| 6 | 63.008 | 3.14 (d, J = 2.1 Hz, 1H) | 7 | 4eq, 7 | 4, 7 |
| 7 | 67.070 | 4.32 (t, J = 2.8 Hz, 1H) | 6, 8 | 6, 8, 15α, 16 | 6, 8 |
| 8 | 33.974 | 1.45 (m, 1H) | 7, 9 | 7, 15α, 18, 19 | |
| 9 | 34.112 | 1.82 (m, 1H) | 8 | 12ax | 6, 7, 19 |
| 10 | 47.459 | | | | 4eq, 19 |
| 11 | 20.488 | 1.35 (ax, dq, J = 14.0, 2.8 Hz, 1H) 2.10 (eq, m, 1H) | | Hax: 18, 19 Heq: 12ax, 19 | 9, 19 |
| 12 | 28.535 | 1.48 (ax, m, 1H), 1.73 (eq, m, 1H) | | Hax: 9, 11eq | 11, 18 |
| 13 | 37.345 | 1.76 (m, 1H) | 18 | 18 | 18 |
| 14 | 90.027 | | | | 8, 15, 16, 18 |
| 15 | 32.957 | 1.71 (α, m, 1H) 1.85 (β, m, 1H) | 16 | Hα: 7, 8, 16, 18 Hβ: 16, 18, 21ax | 16 |
| 16 | 31.462 | 2.17 (m, 2H) | 15 | 7, 15, 21ax | |
| 17 | 109.709 | | | | 8, 15, 16, 21 |
| 18 | 14.470 | 0.95 (d, J = 7.0 Hz, 3H) | 13 | 8, 11ax, 13, 15 | |
| 19 | 14.228 | 1.21 (s, 3H) | | 4ax, 8, 11 | 4ax |
| 20 | 75.065 | | | | 21, 22, 23 |

TABLE 1-continued

NMR data for compound I-1

| Position | $^{13}C$ NMR | HSQC | COSY | ROESY | HMBC |
|---|---|---|---|---|---|
| 21 | 36.926 | 2.40 (ax, d, J = 15.4 Hz, 1H)<br>1.45 (eq, m, 1H) | | Hax: 15β, 16, 27<br>Heq: 27 | 22, 27 |
| 22 | 78.743 | 4.62 (dd, J = 3.5, 1.4 Hz, 1H) | 23 | 23 | 23 |
| 23 | 40.499 | 2.41 (ax, dd, J = 16.1, 1.4 Hz, 1H)<br>2.09 (eq, m, 1H) | 22 | Hax: 22<br>Heq: 22, 28 | 28 |
| 24 | 69.496 | | | | 21eq, 22, 23, 27, 28 |
| 25 | 48.461 | | | | 21, 27, 28 |
| 26 | 176.961 | | | | 21, 22, 27 |
| 27 | 14.041 | 1.14 (s, 3H) | | 21 | 21 |
| 28 | 27.044 | 1.17 (s, 3H) | | 23eq | 23 |

TABLE 2

NMR data for compound I-2

| Position | $^{13}C$ NMR | HSQC | COSY | ROESY | HMBC |
|---|---|---|---|---|---|
| 1 | 201.973 | | | | 3, 19 |
| 2 | 129.287 | 6.10 (dd, J = 9.8, 2.8 Hz, 1H) | 3, 4ax | 3 | 4 |
| 3 | 143.856 | 6.88 (ddd, J = 9.8, 6.3, 2.1 Hz, 1H) | 2, 4eq | 2, 4ax | 4 |
| 4 | 31.978 | 2.96 (ax, dt, J = 18.2, 2.8 Hz, 1H)<br>1.95 (eq, m, 1H) | Hax: 2<br>Heq: 3 | Hax: 19<br>Heq: 3, 6 | 2, 3 |
| 5 | 62.709 | | | | 3, 4ax, 19 |
| 6 | 62.937 | 3.11 (d, J = 2.8 Hz, 1H) | 7 | 4eq, 7 | 4eq, 7 |
| 7 | 67.063 | 4.39 (dd, J = 3.5, 2.8 Hz, 1H) | 6, 8 | 6, 8, 15α, 16α | 6 |
| 8 | 35.278 | 1.68 (m, 1H) | 7, 9 | 7, 15α | 15 |
| 9 | 33.338 | 1.83 (dt, J = 11.9, 3.8 Hz, 1H) | 8, 11 | 12ax | 19 |
| 10 | 47.601 | | | | 4eq, 19 |
| 11 | 21.632 | 1.53 (ax, m, 1H), 2.17 (eq, m, 1H) | 9, 12 | Hax: 19 | 19 |
| 12 | 36.766 | 1.65 (ax, m, 1H), 1.70 (eq, m, 1H) | 11 | Hax: 9 | 18 |
| 13 | 71.219 | | | | 15β, 18 |
| 14 | 88.323 | | | | 15β, 18 |
| 15 | 27.993 | 1.79 (α, m, 1H)<br>2.17 (β, m, 1H) | 16 | Hα: 7, 8, 16α<br>Hβ: 16β, 18 | 16 |
| 16 | 33.686 | 2.07 (α, m, 1H)<br>1.94 (β, m, 1H) | 15 | Hα: 7, 15α<br>Hβ: 15β | 15 |
| 17 | 108.110 | | | | 15β, 16, 20, 21 |
| 18 | 23.916 | 1.21 (s, 3H) | | 15β | |
| 19 | 14.291 | 1.24 (s, 3H) | | 4ax, 11ax | |
| 20 | 40.585 | 2.61 (m, 1H) | 21, 22 | 21eq, 22 | 15β, 16β, 21, 23eq |
| 21 | 26.453 | 2.00 (ax, dd, J = 14.0, 5.6 Hz, 1H)<br>1.59 (eq, m, 1H) | 20 | Hax: 27<br>Heq: 20, 27 | 20, 27 |
| 22 | 74.149 | 4.76 (dt, J = 3.5, 2.1 Hz, 1H) | 20, 23 | 20, 23 | 20, 21 |
| 23 | 40.933 | 2.03 (eq, ddd, J = 15.4, 3.5, 2.1 Hz, 1H)<br>2.23 (ax, dd, J = 15.4, 2.1 Hz, 1H) | 22 | Hax: 22<br>Heq: 22, 28 | 20, 28 |
| 24 | 70.651 | | | | 23, 27, 28 |
| 25 | 47.351 | | | | 21, 27, 28 |
| 26 | 177.626 | | | | 21, 22, 23, 27 |
| 27 | 14.284 | 1.11 (s, 3H) | | 21 | 21eq |
| 28 | 27.399 | 1.14 (s, 3H) | | 23eq | |

TABLE 3

NMR data for compound I-3

| Position | $^{13}$C NMR | HSQC | COSY | ROESY | HMBC |
|---|---|---|---|---|---|
| 1 | 201.805 | | | | 3, 9, 19 |
| 2 | 129.310 | 6.09 (dd, J = 9.8, 3.5 Hz, 1H) | 3, 4ax | 3 | 4 |
| 3 | 143.860 | 6.89 (ddd, J = 9.8, 6.3, 2.1 Hz, 1H) | 2, 4eq | 2 | 4 |
| 4 | 31.899 | 2.95 (ax, dt, J = 18.2, 2.8 Hz, 1H) | Hax: 2 | Hax: 19 | 2, 3, 6 |
|   |   | 1.95 (eq, m, 1H) | Heq: 3 | Heq: 6 |   |
| 5 | 62.910 | | | | 3, 4, 19 |
| 6 | 62.963 | 3.12 (d, J = 2.1 Hz, 1H) | 7 | 4eq, 7 | 7 |
| 7 | 67.973 | 4.34 (t, J = 2.8 Hz, 1H) | 6, 8 | 6, 8, 15α, 16α | 6 |
| 8 | 36.496 | 1.40 (dd, J = 11.9, 3.5 Hz, 1H) | 7, 9 | 7, 15α, 18, 19 | 6, 11ax, 15, 18 |
| 9 | 33.394 | 1.88 (dt, J = 12.6, 2.8 Hz, 1H) | 8 | 11eq | 7, 8, 11, 19 |
| 10 | 47.358 | | | | 2, 4eq, 19 |
| 11 | 23.897 | 1.20 (ax, m, 1H) | 12 | Hax: 12 | 12 |
|   |   | 2.27 (eq, m, 1H) |   | Heq: 9, 12 |   |
| 12 | 37.614 | 1.69 (m, 2H) | 11 | 11, 18 | 18 |
| 13 | 71.066 | | | | 12, 15β, 18 |
| 14 | 89.003 | | | | 12, 15β, 16β, 18 |
| 15 | 27.197 | 1.63 (α, m, 1H) | 16 | Hα: 7, 8, 18 | 16, 18 |
|   |   | 2.31 (β, m, 1H) |   | Hβ: 16β, 18 |   |
| 16 | 33.383 | 2.03 (α, m, 1H) | 15 | Hα: 7 | 15 |
|   |   | 1.97 (β, m, 1H) |   | Hβ: 15β |   |
| 17 | 107.837 | | | | 15β, 16, 20, 21 |
| 18 | 21.871 | 1.53 (s, 3H) | | 8, 12, 15 | 12 |
| 19 | 14.205 | 1.19 (s, 3H) | | 4ax, 8 | 9 |
| 20 | 41.311 | 2.54 (m, 1H) | 21, 22 | 21eq, 22 | 21, 23eq |
| 21 | 26.648 | 2.16 (ax, dd, J = 14.0, 6.3 Hz, 1H) | 20 | Hax: 27 | 27 |
|   |   | 1.55 (eq, dd, J = 14.0, 11.9 Hz, 1H) |   | Heq: 20, 27 |   |
| 22 | 74.415 | 4.73 (dt, J = 3.5, 1.4 Hz, 1H) | 20, 23 | 20, 23 | 20, 21eq, 23eq |
| 23 | 40.578 | 2.40 (ax, dd, J = 15.4, 1.4 Hz, 1H) | 22 | Hax: 22 | 20, 28 |
|   |   | 1.99 (eq, m, 1H) |   | Heq: 22, 28 |   |
| 24 | 70.838 | | | | 21, 22, 23eq, 28 |
| 25 | 47.605 | | | | 21, 23eq, 27 |
| 26 | 177.574 | | | | 21, 22, 27 |
| 27 | 14.265 | 1.14 (s, 3H) | | 21 | 21 |
| 28 | 28.042 | 1.19 (s, 3H) | | 23eq | 23eq |

Table 4 is a comparison of some NMR properties of compounds I-1, I-2, and I-3.

TABLE 4

Comparison of NMR data of compounds I-1, I-2, and I-3

| | Compound I-1 | | Compound I-2 | | Compound I-3 | |
|---|---|---|---|---|---|---|
| Position | $\delta_C$ | $\delta_H$, (J in Hz), (number of protons) | $\delta_C$ | $\delta_H$, (J in Hz), (number of protons) | $\delta_C$ | $\delta_H$, (J in Hz), (number of protons) |
| 1 | 201.825 | | 201.973 | | 201.805 | |
| 2 | 129.261 | 6.08, dd (9.8, 2.8), (1H) | 129.287 | 6.10, dd (9.8, 2.8), (1H) | 129.310 | 6.09, dd (9.8, 3.5), (1H) |
| 3 | 143.748 | 6.86, ddd (9.8, 6.3, 2.8), (1H) | 143.856 | 6.88, ddd (9.8, 6.3, 2.1), (1H) | 143.860 | 6.89, ddd (9.8, 6.3, 2.1), (1H) |
| 4 | 32.064 | 2.95, ax, dt (18.2, 2.8), (1H) | 31.978 | 2.96, ax, dt (18.2, 2.8), (1H) | 31.899 | 2.95, ax, dt (18.2, 2.8), (1H) |
|   |   | 1.93, eq, dd (18.2, 6.3), (1H) |   | 1.95, eq, m, (1H) |   | 1.95, eq, m, (1H) |
| 5 | 62.596 | | 62.709 | | 62.910 | |
| 6 | 63.008 | 3.14, d (2.1), (1H) | 62.937 | 3.11, d (2.8), (1H) | 62.963 | 3.12, d (2.1), (1H) |
| 7 | 67.070 | 4.32, t (2.8), (1H) | 67.063 | 4.39, dd (3.5, 2.8), (1H) | 67.973 | 4.34, t (2.8), (1H) |
| 8 | 33.974 | 1.45, m, (1H) | 35.278 | 1.68, m, (1H) | 36.496 | 1.40, dd (11.9, 3.5), (1H) |
| 9 | 34.112 | 1.82, m, (1H) | 33.338 | 1.83, dt (11.9, 3.8), (1H) | 33.394 | 1.88, dt (12.6, 2.8), (1H) |
| 10 | 47.459 | | 47.601 | | 47.358 | |
| 11 | 20.488 | 1.35, ax, dq (14.0, 2.8), (1H) | 21.632 | 1.53, ax, m, (1H) | 23.897 | 1.20, ax, m, (1H) |
|   |   | 2.10, eq, m, (1H) |   | 2.17, eq, m, (1H) |   | 2.27, eq, m, (1H) |
| 12 | 28.535 | 1.48, ax, m, (1H) | 36.766 | 1.65, ax, m, (1H) | 37.614 | 1.69, m, (2H) |
|   |   | 1.73, eq, m, (1H) |   | 1.70, eq, m, (1H) |   |   |
| 13 | 37.345 | 1.76, m, (1H) | 71.219 | | 71.066 | |
| 14 | 90.027 | | 88.323 | | 89.003 | |

TABLE 4-continued

Comparison of NMR data of compounds I-1, I-2, and I-3

| | Compound I-1 | | Compound I-2 | | Compound I-3 | |
|---|---|---|---|---|---|---|
| Position | $\delta_C$ | $\delta_H$, (J in Hz), (number of protons) | $\delta_C$ | $\delta_H$, (J in Hz), (number of protons) | $\delta_C$ | $\delta_H$, (J in Hz), (number of protons) |
| 15 | 32.957 | 1.71, α (left), m, (1H) | 27.993 | 1.79, α (left), m, (1H) | 27.197 | 1.63, α (left), m, (1H) |
| | | 1.85, β (right), m, (1H) | | 2.17, β (right), m, (1H) | | 2.31, β (right), m, (1H) |
| 16 | 31.462 | 2.17, m, (2H) | 33.686 | 2.07, α (left), m, (1H) | 33.383 | 2.03, α (left), m, (1H) |
| | | | | 1.94, β (right), m, (1H) | | 1.97, β (right), m, (1H) |
| 17 | 109.709 | | 108.110 | | 107.837 | |
| 18 | 14.470 | 0.95, d (7.0), (3H) | 23.916 | 1.21, s, (3H) | 21.871 | 1.53, s, (3H) |
| 19 | 14.228 | 1.21, s, (3H) | 14.291 | 1.24, s, (3H) | 14.205 | 1.19, s, (3H) |
| 20 | 75.065 | | 40.585 | 2.61, m, (1H) | 41.311 | 2.54, m, (1H) |
| 21 | 36.926 | 2.40, ax, d (15.4), (1H) | 26.453 | 2.00, ax, dd (14.0, 5.6), (1H) | 26.648 | 2.16, ax, dd (14.0, 6.3), (1H) |
| | | 1.45, eq, m, (1H) | | 1.59, eq, m, (1H) | | 1.55, eq, dd (14.0, 11.9), (1H) |
| 22 | 78.743 | 4.62, dd (3.5, 1.4), (1H) | 74.149 | 4.76, dt (3.5, 2.1), (1H) | 74.415 | 4.73, dt (3.5, 1.4), (1H) |
| 23 | 40.499 | 2.41, ax, dd (16.1, 1.4) (1H) | 40.933 | 2.03, eq, ddd (15.4, 3.5, 2.1), (1H) | 40.578 | 2.40, ax, dd (15.4, 1.4), (1H) |
| | | 2.09, eq, m, (1H) | | 2.23, ax, dd (15.4, 2.1), (1H) | | 1.99, eq, m, (1H) |
| 24 | 69.496 | | 70.651 | | 70.838 | |
| 25 | 48.461 | | 47.351 | | 47.605 | |
| 26 | 176.961 | | 177.626 | | 177.574 | |
| 27 | 14.041 | 1.14, s, (3H) | 14.284 | 1.11, s, (3H) | 14.265 | 1.14, s, (3H) |
| 28 | 27.044 | 1.17, s, (3H) | 27.399 | 1.14, s, (3H) | 28.042 | 1.19, s, (3H) |

Compound I-1 was isolated as white crystalline needles, whose molecular formula was determined to be $C_{28}H_{36}O_8$ by high resolution mass spectrometry (m/z 501.2493 $[M+H]^+$, 523.2311 $[M+Na]^+$). Analysis of $^1H$, $^{13}C$, and HSQC spectra revealed four methyl, seven methylene, eight methane, and nine quarternary carbons, and suggested 2 two hydroxyl groups, consistent with this formula. Subsequent 2D analysis (gCOSY, ROESY, and HMBC, see Table 1) lead to the structure determination and the complete $^{13}C$ and $^1H$ NMR assignment is summarized in Table 4. Some structural features included two olefenic protons H-2 (δ 6.08, dd, J=9.8, 2.8 Hz, 1H) and H-3 (δ 6.86, ddd, J=9.8, 6.3, 2.8 Hz, 1H) conjugated to carbonyl carbon C-1 (δ 201.825) consistent with an α,β-unsaturated ketone, a likely C-5,6 epoxide, and the characteristic ketal carbon C-17 (δ 109.709). Another structural feature centered around carbonyl carbon C-26 (δ 176.961) and was indicative of an isolated bridged δ-lactone moiety, containing two methyl and two hydroxyl groups. The structure and stereochemistry of compound I-1 was determined by X-ray crystallography (FIG. 5) and ROESY 2D NMR analysis (see Table 1). Compound I-1 contains 28 carbons in which C-22 and C-26 have been oxygenated to form a δ-lactone, possibly putting it into the class of steroids known as withanolides. If so classified, compound I-1 could be the first withanolide having a disconnection between C-13 and C-17, which typically forms ring D of the ergostane skeleton. FIG. 4 shows that compound I-1 has in vitro cytotoxic activity against DU145 ($GI_{50}$=~1.5 μg/mL) and RWPE-1 ($GI_{50}$=~1.2 μg/mL) cells.

Figure 5:
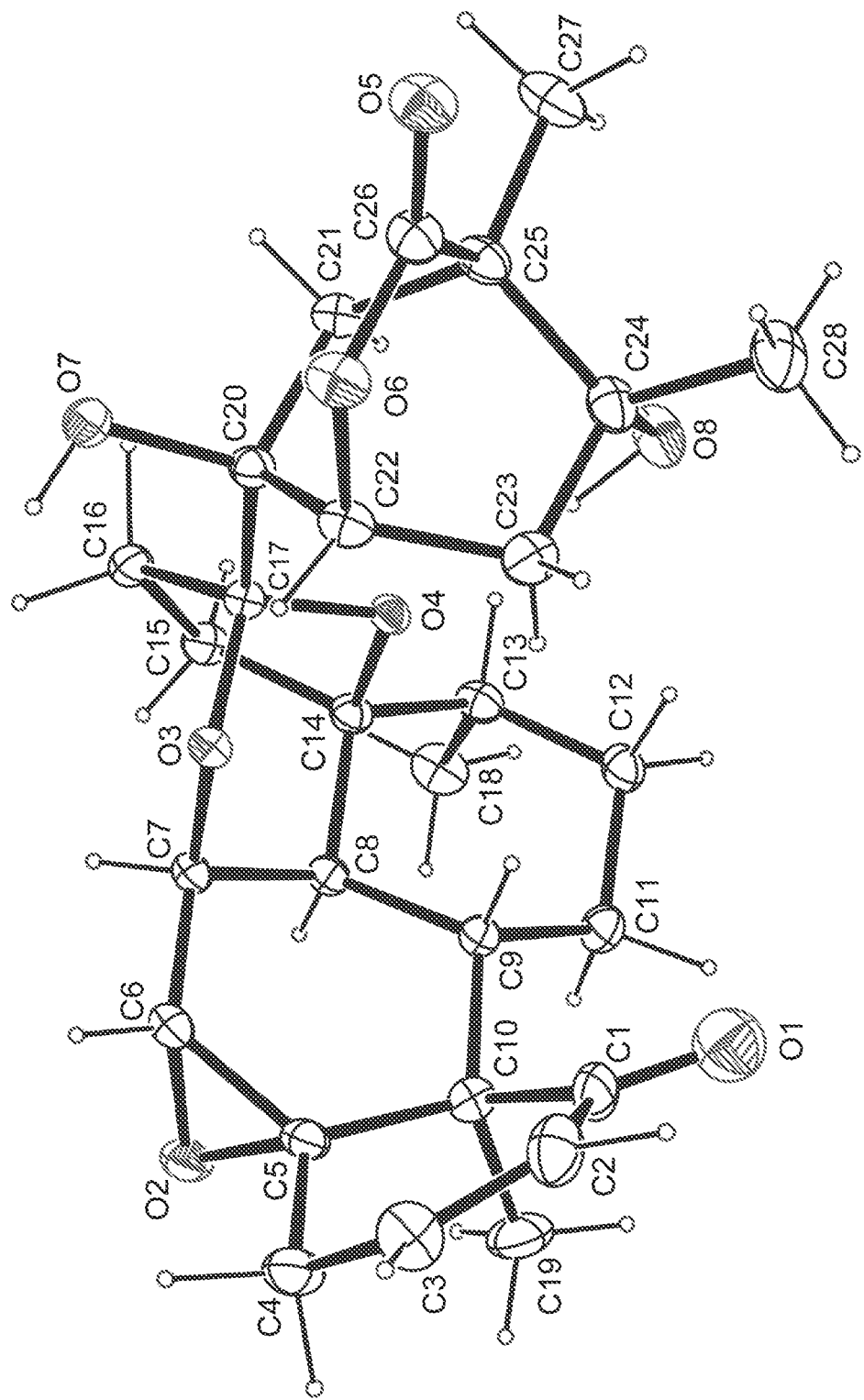
FIG. 5. An ORTEP-3 diagram of compound I-1 showing 40% ellipsoids. H atoms are shown as small spheres of arbitrary radii. Selected bond lengths (Å) and angles (deg): O1-C1) 1.178 (5), O5-C26) 1.204 (4), O7-C20) 1.418 (3), O8-C24) 1.437 (4), C13-C18) 1.535 (4), C12-C13-C18) 112.5 (3).
Figure 6:
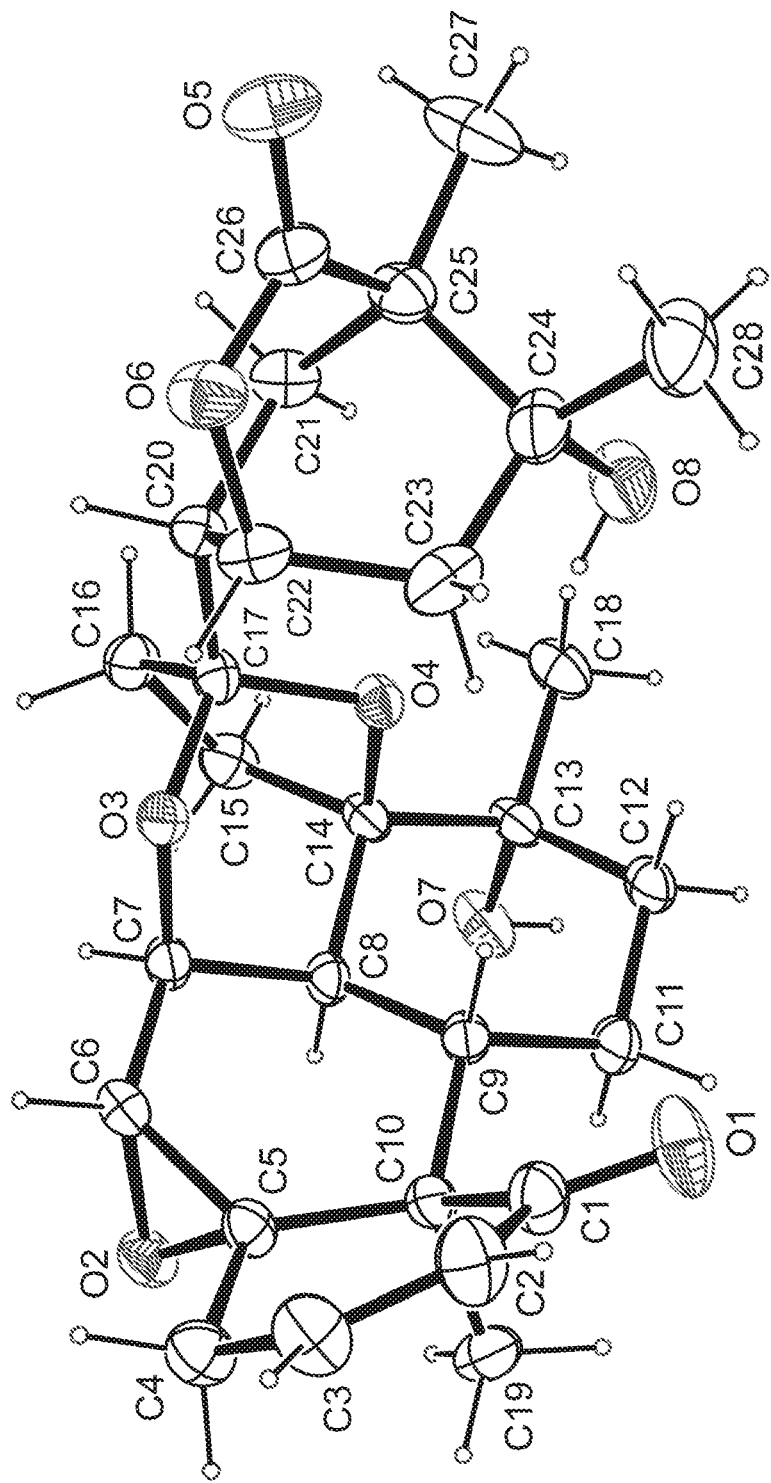
FIG. 6. An ORTEP-3 diagram of Compound I-2 showing 40% ellipsoids. H atoms are shown as small spheres of arbitrary radii. Selected bond lengths (Å) and angles (deg): O1-C1) 1.188 (5), O5-C26) 1.218 (7), O7-C13) 1.433 (5), C13-C18) 1.527 (6), O7-C13-C18) 110.4 (4), C12-C13-C18) 109.4 (4).

Compounds I-2 and I-3 were also isolated as white needles, and both were found to have the molecular formula of $C_{28}H_{36}O_8$ by high resolution mass spectrometry (m/z 523.2311 $[M+Na]^+$ for compound I-2; m/z 523.2313 $[M+Na]^+$ for compound I-3), indicating both are isomers of compound I-1. After analysis of the NMR data (see Tables 2-4), we found that in the structures of compounds I-2 and I-3, C-13 is hydroxylated instead of at C-20 in compound I-1, and that compounds I-2 and I-3 differed from each other only at the stereochemistry at C-13 (FIG. 5 and FIG. 6). As with compound I-1, compounds I-2 and I-3 also contained the bridged δ lactone moiety and the disconnection between C-13 and C-17. Compound I-2 was subjected to X-ray crystallography, thus confirming the aforementioned C-13 hydroxyl and the absence of a hydroxyl on C-20 (FIG. 6), and further demonstrated that with the exception of the orientation of the C-13 methyl group, the overall conformation of compounds I-1 and I-2 were similar (FIG. 5 and FIG. 6). A single crystal of compound I-3 suitable for X-ray crystallography was not obtained. However, the ROESY 2D NMR comparison between compound I-2 and I-3 confirmed that the C-18 methyl of compound I-3 is located axially and the hydroxyl group is located equatorially on C-13 of compound I-3, while in compound I-2 the C-18 methyl is equatorial on C-13 and the hydroxyl is axial. Accordingly, $CH_3$-18 shows a strong correlation with H-8 and H-15 (both α and β) in compound I-3. However, $CH_3$-18 of compound I-2 has only a single interaction with H-15β observed in the ROESY spectra. A similar interaction was observed in Compound I-1; CH3-18 has interaction with H-8 and H-15 (α and β) on ROESY, indicating the preferred axial orientation of the methyl group in both compounds I-1 and I-3.

FIG. 4 shows that the $GI_{50}$ values for compounds I-2 and I-3 were similar. The $GI_{50}$ values for compound I-2 were 3.0 μg/mL and 3.4 μg/mL against RWPE-1 and DU145, respectively. The $GI_{50}$ values for compound I-3 were 3.3 μg/mL and 3.0 μg/mL against RWPE-1 and DU145, respectively.

EXAMPLE SET 2

General Experimental Procedure. Compound I-1 was isolated as described in Example Set 1, above. For samples of compound I-1 used in Example Set 2, HPLC and NMR indicated a purity of at least 95%. All experiments described in Example Set 2 were repeated at least two or three times. All MTT assays were performed according to Bates et al. "G-Rich Oligonucleotides for Cancer Treatment" Chapter 21 of Methods in Molecular Biology, Gene Therapy of Cancer, Wolfgang Walther and Ulrike S. Stein (eds.), Vol. 542, 2009, Humana Press.

Cell Culture and Treatment. All cells were obtained from ATCC and were grown in a humidified incubator at 37° C. with 5% $CO_2$. DU145 (hormone-refractory prostate cancer) cells were grown in DMEM and PC3 (hormone-refractory prostate cancer) were grown in F-12K medium supplemented with 10% fetal bovine serum (FBS; Life Technologies), 62.5 μg/mL penicillin and 100 μg/mL streptomycin (Hyclone Laboratories, Logan, Utah). Cells ($1 \times 10^6$) in fresh complete culture medium were plated on 10 cm diameter tissue dishes for 18 h. Cells were treated by addition of compound I-1 directly to the culture medium to give the final concentration indicated in the figure legends. Cells for biochemical analyses cells were lysed in lysis buffer (150 mM NaCl, 2 mM EDTA, 50 mM Tris-HCl, 0.25% deoxycholic acid, 1% octylphenoxypolyethoxyethanol (IGEPAL CA-630), pH 7.5) containing protease and phosphatase inhibitor cocktails (Calbiochem, Billerica, Mass.) for 10 min at 4° C. and then cleared by centrifugation at 16,000 g for 10 min at 4° C. All protein concentrations were determined using the bicinchoninic acid (BCA) protein assay (Pierce, Rockford, Ill.).

Clonogenic Assay. Cells in fresh complete medium were plated at very low density ($3 \times 10^2$ per well) into six-well plates for 18 h. After complete adhesion, cells were treated with compound I-1 by adding directly to the medium to give the concentration indicated in the figures. Cells were allowed to grow until visible colonies formed (10 days). Cell colonies were fixed with 4% paraformaldehyde in PBS (phosphate-buffered saline), stained with 0.25% crystal violet in 25% methanol, washed and air-dried.

Flow cytometric assays of cell cycle and cell death. Cells in fresh complete medium were plated ($2 \times 10^5$ per well) into six-well plates for 18 h. After complete adhesion, cells were treated as indicated in the figures and harvested by trypsinization. For cell cycle distribution, cells were fixed, and stained with propidium iodide using the Cycle Test Plus kit (Becton Dickinson). For cell death detection, cells were stained with Annexin-V-FITC and propidium iodide using the Apoptosis Detection Kit (BD Biosciences), according to the manufacturer's instructions. Cells were then analyzed by flow cytometry using a FACScalibur cytometer (BD Biosciences, Mountain View, Calif.) and FlowJo program (Tree Star, Inc., Ashland, Oreg.).

DNA Fragmentation assay. After indicated treatment, cells ($2 \times 10^6$) were collected (trypsinized and floating cells in the supernatant). DNA was extracted as described. Briefly, cells were lysed in 1% NP-40, 20 mM EDTA, 50 mM Tris-HCl, pH 7.5 for 20 min on ice and were clarified by centrifugation at 16,000 g for 10 min at 4° C. Lysates were incubated with 0.5% SDS (W/V), pH 8.0, containing 0.5 mg/ml RNAse A (Invitrogen, Grand Island, N.Y.) for 1 h at 37° C., and subsequently with 0.25 mg/ml proteinase K (Promega, Madison, Wis.) for 1 h at 50° C. Afterwards, the lysates were subject to one round of extraction using phenol:chloroform:isoamyl alcohol (25:24:1; pH 7.4) and DNA was precipitated from the cell lysates by adding ammonium acetate at a final concentration of 3 M and one volume of ice cold isopropanol followed by 1 h incubation on ice. DNA was pelleted by centrifugation at 16,000 g for 1 h at 4° C. before being washed in cold 80% (V/V) ethanol and air-dried. The DNA pellet was resuspended in Tris-buffer (10 mM Tris-HCl and 1 mM EDTA (pH 8.0)). The samples were subjected to electrophoresis on 1.8% agarose gel; the DNA was stained with ethidium bromide and then visualized using ultraviolet light (302 nm).

Immunofluorescence microscopy. Cells ($2.5 \times 10^4$) in fresh complete culture medium were plated on 18 mm diameter glass cover slips for 18 h. The medium was replaced with complete medium containing 10 μM compound I-1 or an equivalent volume of vehicle (DMSO) and incubated for 24 or 48 h. After incubation, cells were washed 3 times with ice-cold PBS, fixed in 4% paraformaldehyde in PBS for 30 min at room temperature, and washed three times with PBS. Cells were permeabilized for 1 min in PBS containing 0.1% Triton X-100, and washed three times with PBS. Nonspecific binding sites were blocked for 30 min with 3% BSA in PBS, and the fixed cells were incubated for 60 min with anti-α-tubulin (11H10) antibody conjugated to Alexa Fluor® 488 (Cell Signaling Technology, Inc., Danvers, Mass.). Antibody dilution was carried out using PBS containing 3% BSA. After washing, the cover slips were mounted on glass slides with ProLong Antifade (Molecular Probes) according to the manufacturer's directions. Immunofluorescence was documented with a Nikon A1 inverted confocal laser-scanning microscope (Nikon Instruments, Inc., Melville, N.Y.) equipped with an Omnichrome argon-krypton laser. Images were obtained with a 40X Plan-Neo 6 oil immersion objective (1.3 NA).

Immunoblotting. Samples were resolved by 4-20% precast linear gradient SDS-Tris polyacrylamide gel electrophoresis (Bio-rad Bio-Rad Laboratories, Hercules, Calif.) and then electrotransferred onto polyvinylidine fluoride membranes (Millipore, Bedford, Mass.) in Tris-glycine buffer containing 20% methanol. Membranes were incubated in blocking buffer containing 5% nonfat dry milk (Carnation; Nestle, Glendale, Calif.) and 0.1% Tween 20 in PBS for one hour at room temperature. Subsequently, membranes were probed with anti-PARP-1 (D-1) monoclonal antibody (Santa Cruz Biotechnology, Santa Cruz, Calif.) at 200 ng/ml in blocking buffer overnight at 4° C. After washing six times with PBS containing 0.1% Tween 20, membranes were incubated with HRP (horseradish peroxidase)-conjugated goat anti-mouse IgG for 1 h at room temperature and were washed six more times with PBS containing 0.1% Tween 20. Antibody-reactive proteins were detected using a chemiluminescence substrate (SuperSignal; Pierce, Rockford, Ill.) according to the manufacturer's instructions. A similar protocol was used to detect activated Caspase-3 using anti-cleaved Caspase-3 rabbit antibody (Cell Signaling Technology, Inc., Danvers, Mass.) at a dilution of 1:1000.

Figure 7:
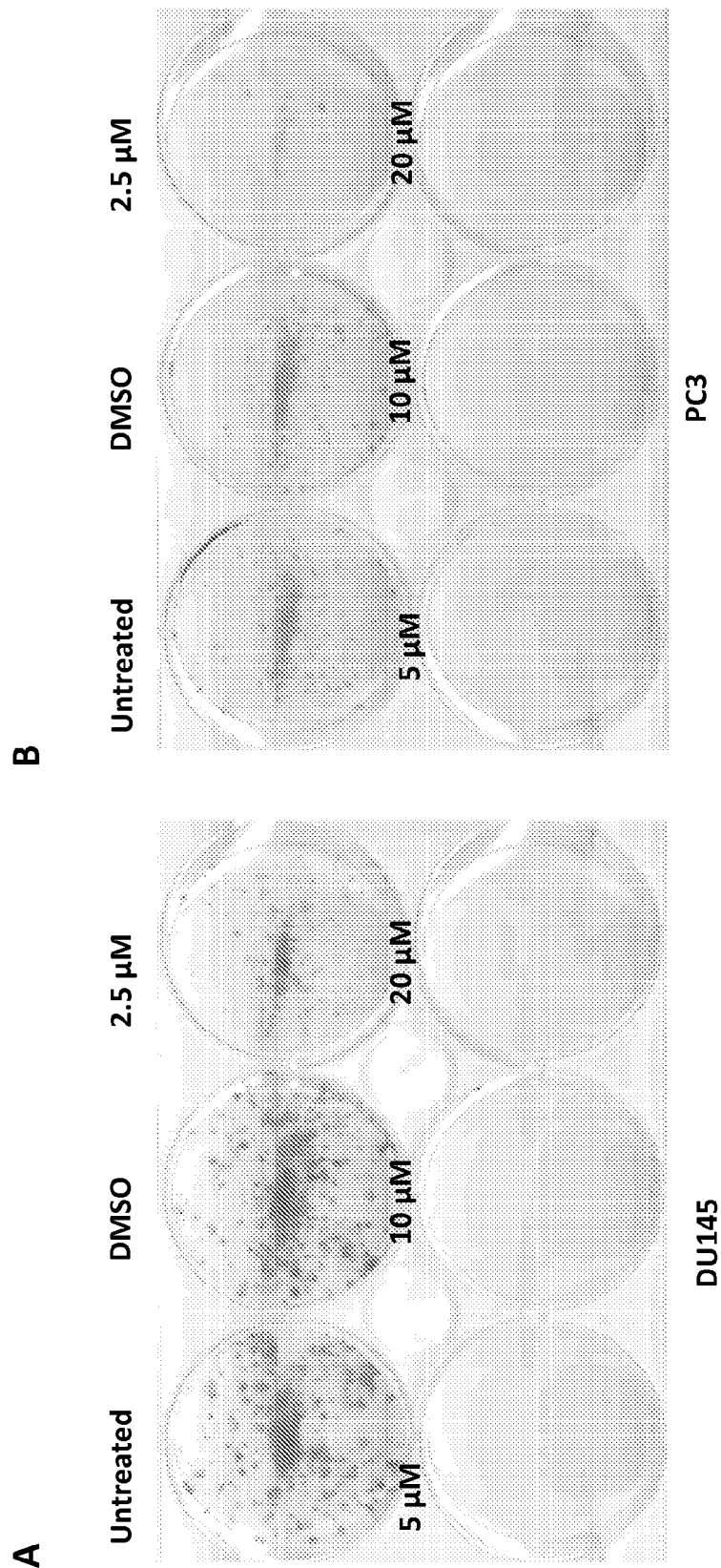
FIG. 7. Clonogenic assays in prostate cancer cells treated with compound I-1. Prostate cancer cells, DU145 (A) or PC3 (B), were plated at very low density in 6-well plates and incubated 18 h at 37° C. Cells were treated by addition of various concentrations of compound I-1 or with an equivalent volume of vehicle (DMSO), or were left untreated. After 10 days of treatment, cells were washed with cold PBS, fixed with paraformaldehyde, and stained with crystal violet solution.
Figures 8A, 8B:
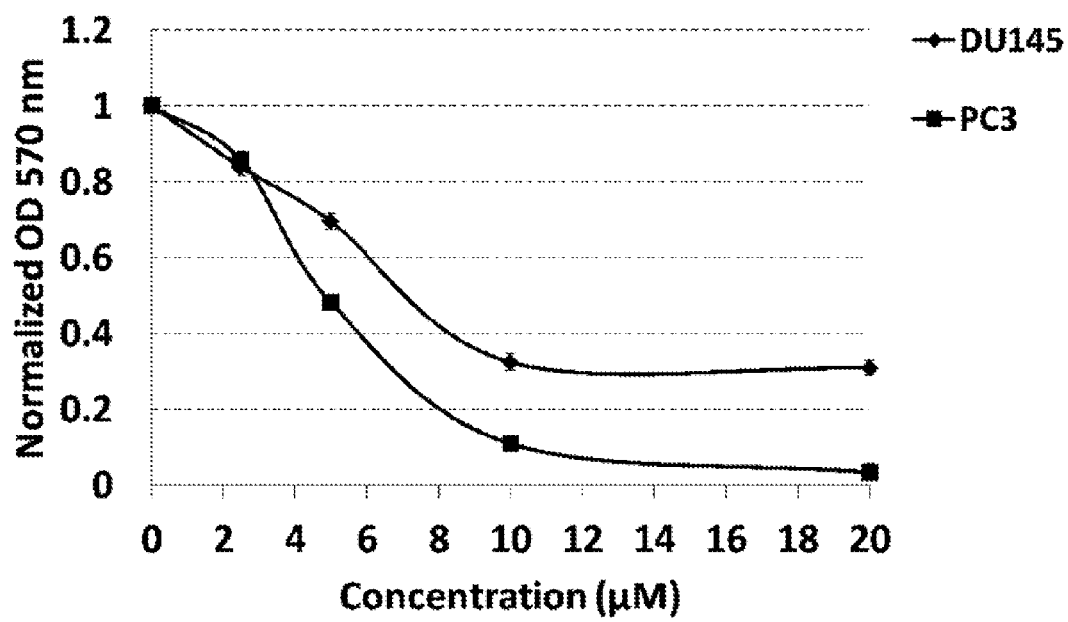
FIG. 8. Cell proliferation assay. (A) DU145 or PC3 prostate cancer were plated at a density of 1,500 cells per well in 96-well plates and incubated 18 hours at 37° C. to allow adherence. They were untreated or treated by addition of different concentrations of compound I-1 (which were added directly to the medium) or vehicle (DMSO), and proliferation was measured using a 3-(4,5-dimethylthiazol-2-yl)-2,5-diphenyltetrazolium bromide MTT assay after 3 days of treatment. Points, mean of triplicate normalized samples to vehicle sample; bars, SE. (B) $GI_{50}$ after 3 days of treatment. (C) Prostate cancer cells (DU145 or PC3) or a non-malignant epithelial cells (RWPE-1) were plated at a density of 1,000 cells per well in 96-well plates and incubated 18 hours at 37° C. to allow adherence. They were untreated or treated by addition of different concentrations of compound I-1 (added directly to the medium) or vehicle (DMSO), and proliferation was by MTT assay after 5 days of treatment. Points, mean of triplicate normalized samples to vehicle sample; bars, SE.
Figure 8C:
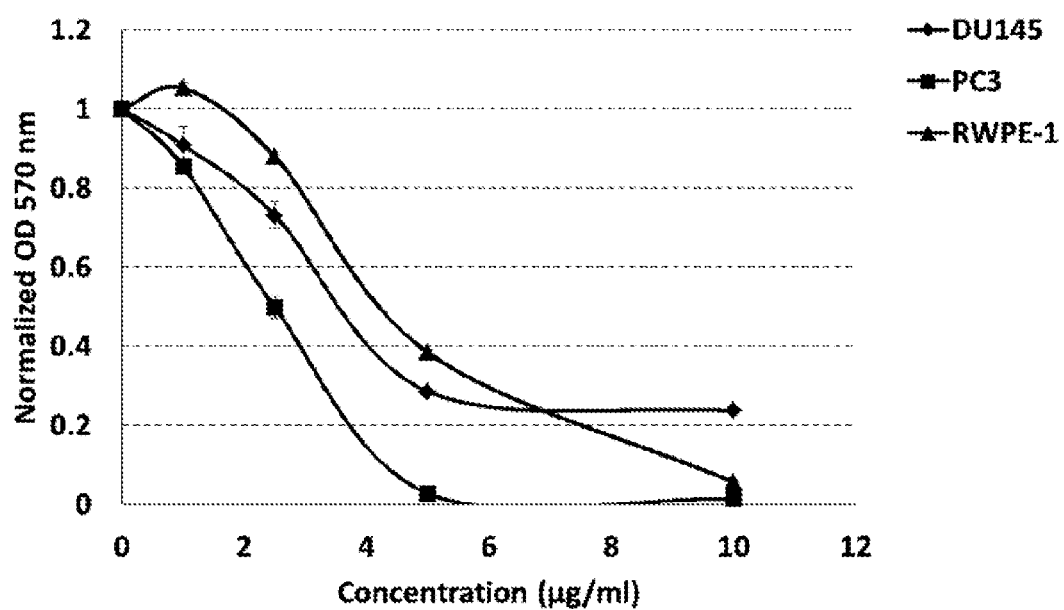

Compound I-1 inhibits clonogenic survival of prostate cancer cells. To determine if compound I-1 can compromise the colony-forming capacity of prostate cancer cells, we measured its activity at 2.5, 5, and 10 μM in both DU145 and PC-3 cells using clonogenic assays. Inhibitory effects were seen at 2.5 μM. Compound I-1 blocked the capacity of single cancer cells to generate colonies for both prostate cancer cell lines at a concentration of 5 μM or higher (FIG. 7). Compound I-1 appeared to have the maximum antiproliferative activity at a concentration of 10 μM on two prostate cancer cell lines (DU145 and PC3) after three days of treatment (FIG. 8). After five days of treatment, compound I-1 appeared to selectivity inhibit cancer cell growth as compared to non-malignant cell growth (FIG. 8C). A concentration of 10 μM was chosen to investigate the mechanism of compound I-1.

Figure 9A:
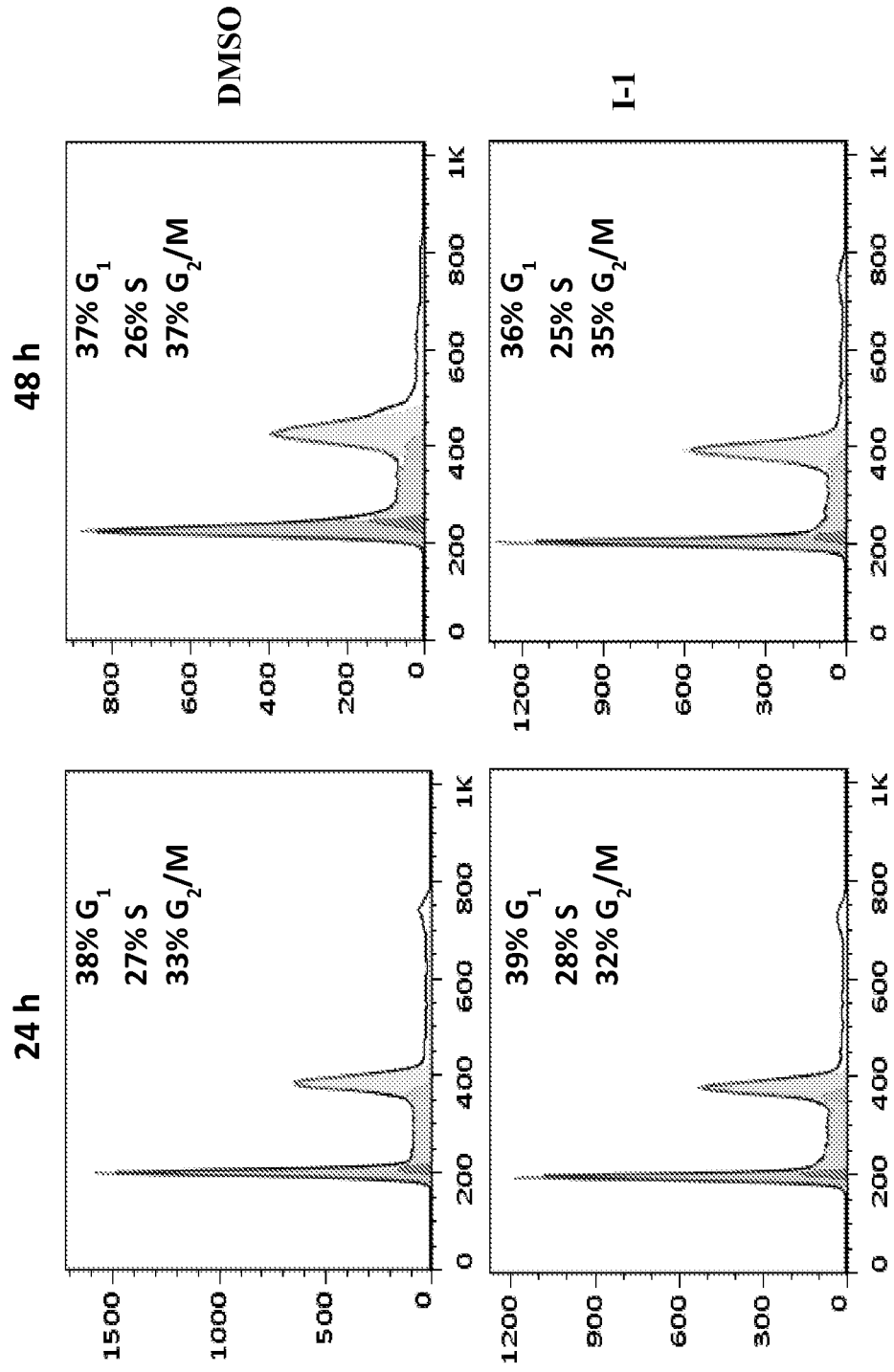
FIG. 9. Effect of compound I-1 at 5 μM on cell cycle and apoptosis. DU145 cells were incubated in the presence of compound I-1 (5 μM) or vehicle (DMSO) for the time indicated in the figure. Cells were then harvested by trypsinization. (A) For flow cytometric analysis of cell cycle parameters, cells were fixed, and stained with propidium iodide. Each histogram indicates the percent of cells in $G_1$, S, and $G_2$/M phases of the cell cycle. Data were gated to exclude apoptotic cells for these calculations. (B) For apoptosis detection, cells were incubated with FITC-conjugated Annexin V and propidium iodide. Flow cytometric analysis was performed and the histogram for each sample was split into four quadrants to indicate: viable cells (lower left quadrant), apoptotic cells (lower right quadrant), necrotic cells (upper left quadrant), and necrotic/late apoptotic cells (upper right quadrant).

Compound I-1 induces G2/M cell arrest. To investigate whether compound I-1 could induce cell cycle perturbations in prostate cancer cells, flow cytometric analyses of propidium iodide stained nuclei cells were performed. Cell cycle parameters were compared for DU145 cells that had been incubated for 24 h or 48 h with compound I-1 (10 μM or 5 μM), with vehicle as control (DMSO), or without treatment (untreated). Cell cycle parameters were not perturbed in DU145 cells treated with compound I-1 at a concentration of 5 μM (FIG. 9A). However, as shown in FIG. 10, following 24 h of treatment with compound I-1 at a concentration of 10 μM, there was a decrease in the fraction of cells in phase (8% compared to 39% in untreated cells) and an increase in the proportion of cells in S phase (37% compared to 28%) and $G_2$/M phases (49% compared to 31%), By 48 h, the percentage of cells in S phase cell had decreased in samples treated with compound I-1 and there was a concomitant increase in the fraction of cell in $G_2$/M (66% compared to 36% in untreated cells). We also observed an additional peak to the right of the G2/M peak, consistent with a population of aneuploid cells that contain more than 4n DNA. This peak may represent a population of cells that have escaped mitotic arrest and continued to replicate as multinuclear cells without dividing (i.e., endoreduplication), or it may be that there was a small fraction of tetraploid cells already present in the culture, which underwent G2/M arrest resulting in cells with ~8n DNA. We found that compound I-1, at a concentration of 10 μM, was also able to cause G2/M arrest in PC3 cells (FIG. 11), indicating that the activity of compound I-1 was not just DU145 cell type specific. We conclude from these results that compound I-1 inhibits cell cycle progression at the $G_2$/M phase.

Figure 9B:
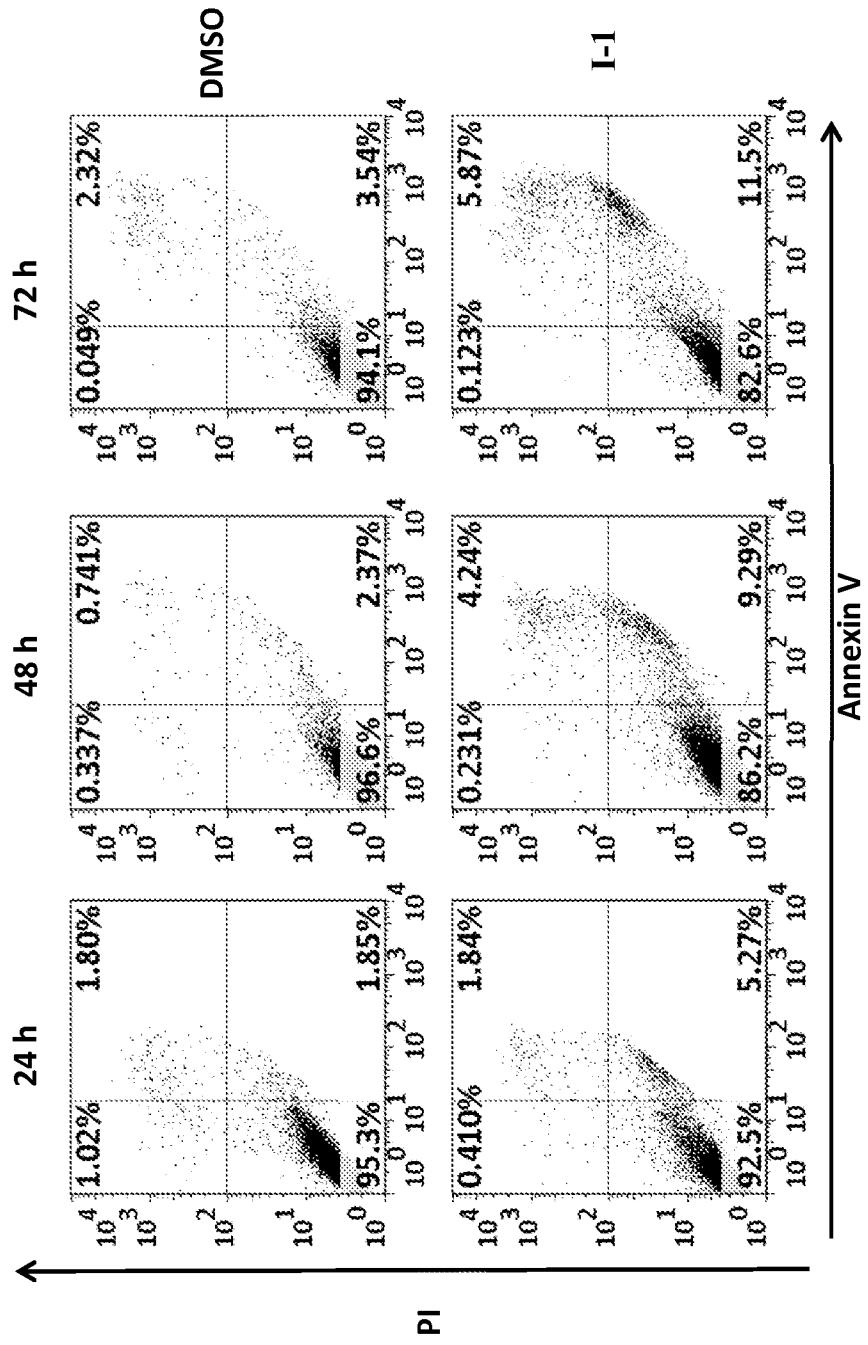
Figure 12:
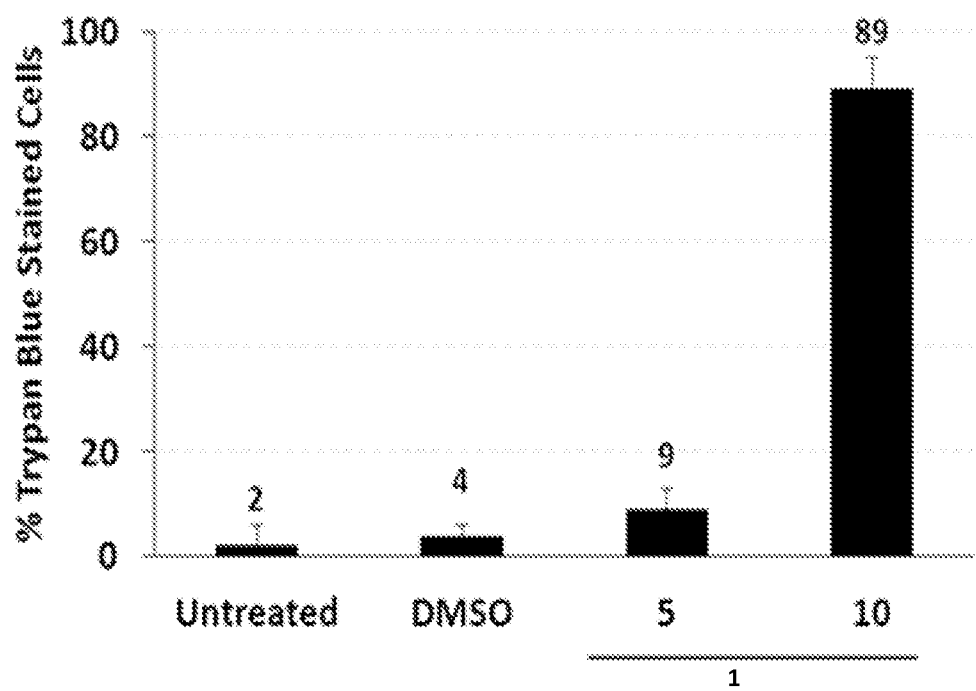
FIG. 12. Trypan blue exclusion assay to determine cell death. DU145 prostate cancer cells were left untreated or treated with 10 μM compound I-1 or with vehicle (DMSO) for 72 h. After treatment, all cells (both adherent and floating) were harvested, stained with trypan blue, and counted immediately to determine the percentage of non-viable cells (stained blue). Columns represent the mean of three independent experiments, bars represent standard error, and numbers above each column represent the percentage of blue cells in the sample.
Figure 13A:
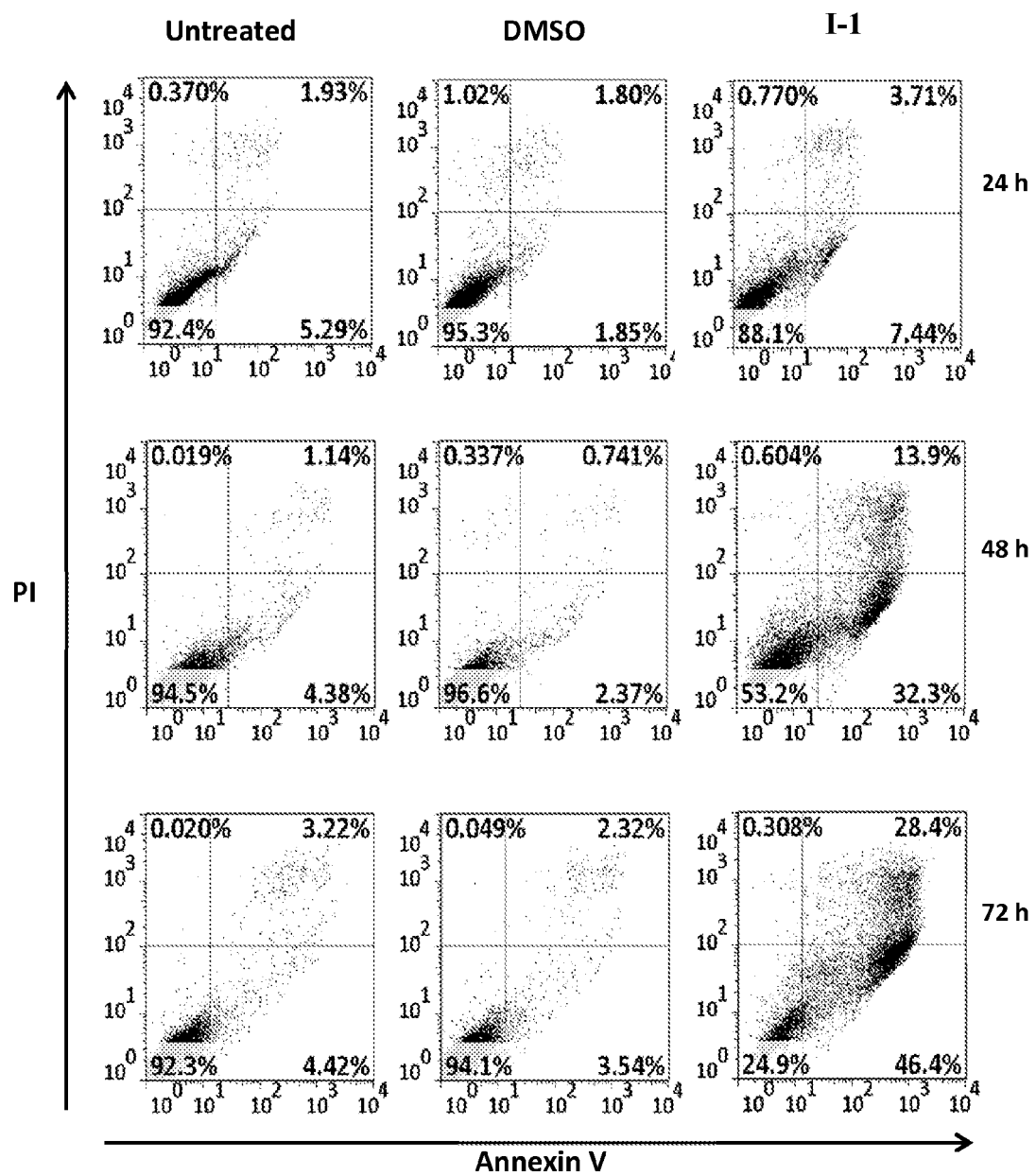
FIG. 13. Assays to detect apoptosis in DU145 cells. Prostate cancer cells were left untreated (−) or treated with 10 μM compound I-1 or with vehicle (DMSO) for the time indicated in the figure. (A) After treatment, cells were harvest by trypsinization, washed with PBS, and then incubated with FITC-conjugated Annexin V and propidium iodide. Flow cytometric analysis was performed. The histogram for each sample was split into four quadrants to indicate: viable cells (lower left quadrant), apoptotic cells (lower right quadrant), necrotic cells (upper left quadrant), and necrotic/late apoptotic cells (upper right quadrant). (B) After treatment, cells were lysed and total lysates were analyzed for cellular apoptotic markers by immunoblotting using anti-PARD-1 or antibodies specific to the activated form of Caspase-3 (cleaved Caspase-3). Anti-GAPDH-1 antibody was used as loading control. (C) Some cells were harvested by trypsinization, washed with PBS, and total DNA was extracted then analyzed on a 1.8% agarose gel. M indicates DNA size marker (base pairs).

Compound I-1 promotes cell death by apoptosis. Because prolonged cell cycle arrest can cause induction of cell death, we next investigated the viability of prostate cancer cells treated with compound I-1. To begin, we used the trypan blue exclusion assay, which is based on the principle that live cells will exclude membrane-impermeable dyes such as trypan blue, whereas trypan blue will get inside the dead cells and stain them. This test showed that almost 90% of DU145 cells were dead after treatment with 1 (10 μM) for 72 h (FIG. 12). To determine whether apoptosis (programmed cell death) is the cause of cell death induced by compound I-1, we examined the cells for biochemical and morphological markers of apoptosis. Cells undergoing apoptosis specifically translocate the membrane phospholipid phosphatidylserine (PS) from the inner face of the plasma membrane to the cell surface; therefore, apoptotic cells can be identified by the presence of PS on the cell surface. Detection of PS is achieved by staining with a fluorescent conjugate of Annexin V, a protein that has a high affinity for PS, followed by flow cytometry analysis. Cells are stained in parallel with propidium iodide (PI), which can only enter the cell when the plasma membrane is damaged. This allows early apoptotic cells (positive for PS, but negative for PI) to be distinguished from late apoptotic and necrotic cells (positive for both PS and PI). FIG. 13A and FIG. 10B show that DU145 prostate cancer cells receiving control treatments (untreated or DMSO) possess a baseline apoptotic cell population of less than 4%. DU145 cells treated with compound I-1 at a concentration of 5 μM for 24 h, 48 h, and 72 h just reach a light increase in the apoptotic population of 5.2%, 9.2%, and 11.5% respectively (FIG. 9B). After 24 h, DU145 cells treated with compound I-1 at a concentration of 10 μM showed also a small increase in the apoptotic population (7.4%). However, after 48 and 72 h, compound I-1 induced an increase in the apoptotic cell population to 32.3% and 46.4%, respectively. Furthermore, a population of late apoptotic/necrotic cells (28.4%) was also observed after 72 h treatment with compound I-1 (10 μM) (FIG. 13A).

Figure 11A:
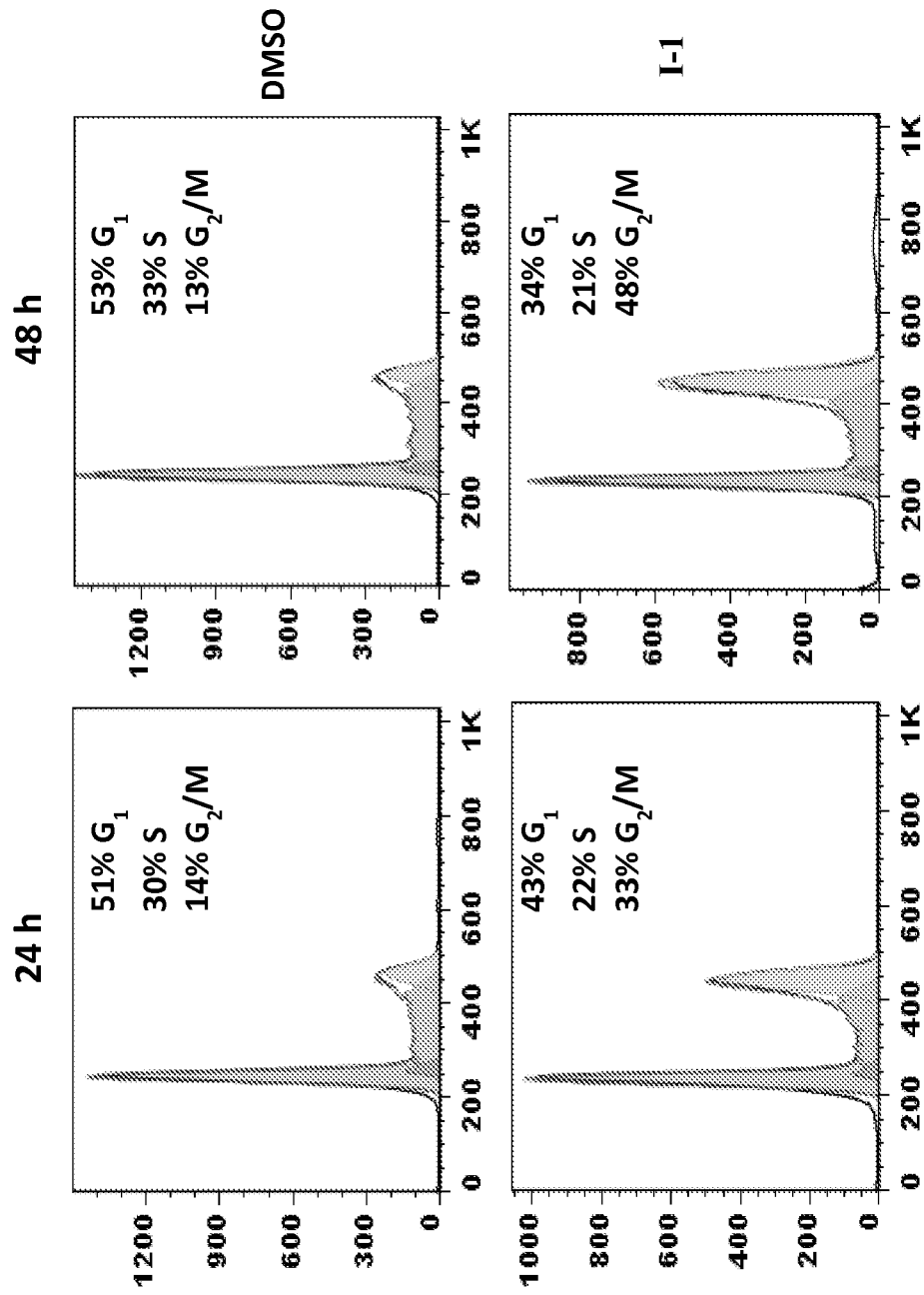
FIG. 11. Compound I-1 induces cell cycle arrest and apoptosis in PC3 cells. Prostate cancer cells were left untreated (−) or treated with compound I-1 (10 μM) or with vehicle (DMSO) for the time indicated in the figure. (A) For flow cytometric analysis of cell cycle parameters, cells were fixed, and stained with propidium iodide. Each histogram indicates the percent of cells in $G_1$, S, and $G_2$/M phases of the cell cycle. Data were gated to exclude apoptotic cells for these calculations. (B) After treatment, cells were lysed and total lysates were analyzed for cellular apoptotic markers by immunoblotting using anti-PARP-1 or anti-cleaved Caspase-3 antibodies. Anti-GAPDH-1 antibody was used as loading control. (C) Some 48 h-treated PC3 cells were harvest by trypsinization, washed with PBS, and total DNA was extracted then analyzed on a 1.8% agarose gel. M indicates DNA size marker (base pairs).
Figure 13B:
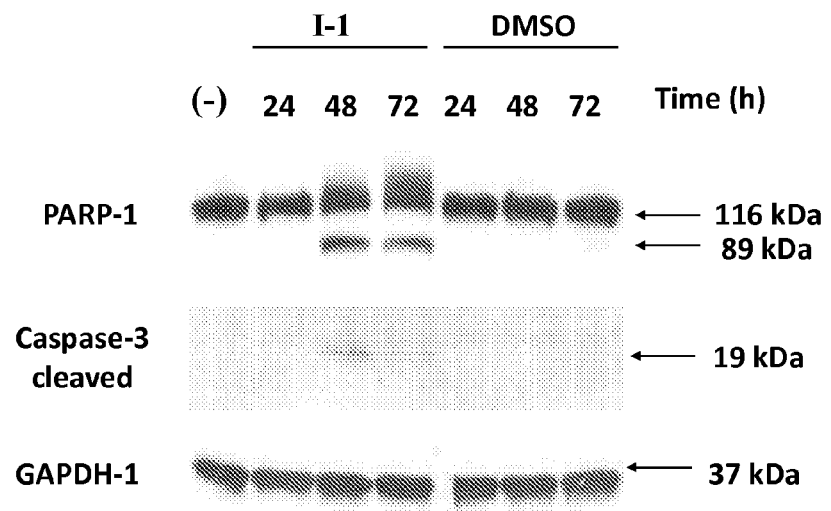

Next, to further confirm that compound I-1 induces apoptosis in prostate cancer cells, we evaluated key apoptotic molecular markers. Caspase-3 activation and poly(ADP-ribose) polymerase (PARP-1) cleavage into fragments of 89 and 24 kDa are considered as hallmarks of apoptosis. Caspase-3 activity can be a factor for the proteolytic cleavage of some proteins during apoptosis, including PARP-1. Activation of caspase-3 can require proteolytic processing of its inactive zymogen into activated 17/19 and 12 kDa fragments. Therefore, we examined whether compound I-1 might induce caspase-3 activation (i.e., caspase-3 cleavage) and PARP-1 cleavage. Protein extracts from DU145 cells were collected at different time points after compound I-1 treatment, and equal amounts of protein extract were examined by immunoblotting with anti-cleaved caspase-3 and anti-PARP-1 antibody. Cell extracts from control cells (untreated or DMSO) showed no detectable activation of caspase-3 (cleaved caspase-3) and PARP-1 existed predominantly as the full-length product (116 kDa) (FIG. 13B). However, activated caspase-3 and cleavage of PARP-1 protein (additional band at 89 kDa) were detected in extracts from cells treated with compound I-1 (10 μM) for 48 h and 72 h. Caspase-3 activation and PARP-1 cleavage could not be detected in protein extracts from cells treated for time periods shorter than 48 h (FIG. 13B). Compound I-1 was also able to induce the activation of caspase-3 and the cleavage of PARP-1 in PC3 cells (FIG. 11B)

Figure 13C:
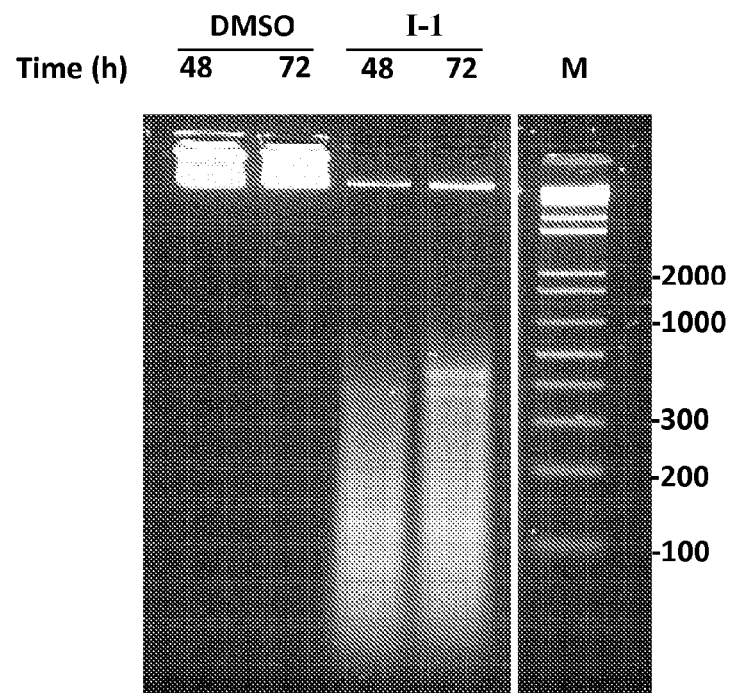

For further evidence of apoptosis, we tested whether compound I-1 might induce the cleavage of chromatin into oligonucleosome-length DNA fragments, which appear as "DNA ladder" on agarose gels, because this is another biochemical hallmark of apoptosis. For both DU145 cells (FIG. 13C) and PC3 cells (FIG. 11C), the characteristic "DNA ladder" was seen only when cells were treated with compound I-1 (10 μM) for the time indicated in the figures, but not in the control cells (DMSO treated), indicating that compound I-1 induces apoptosis.

Figure 14:
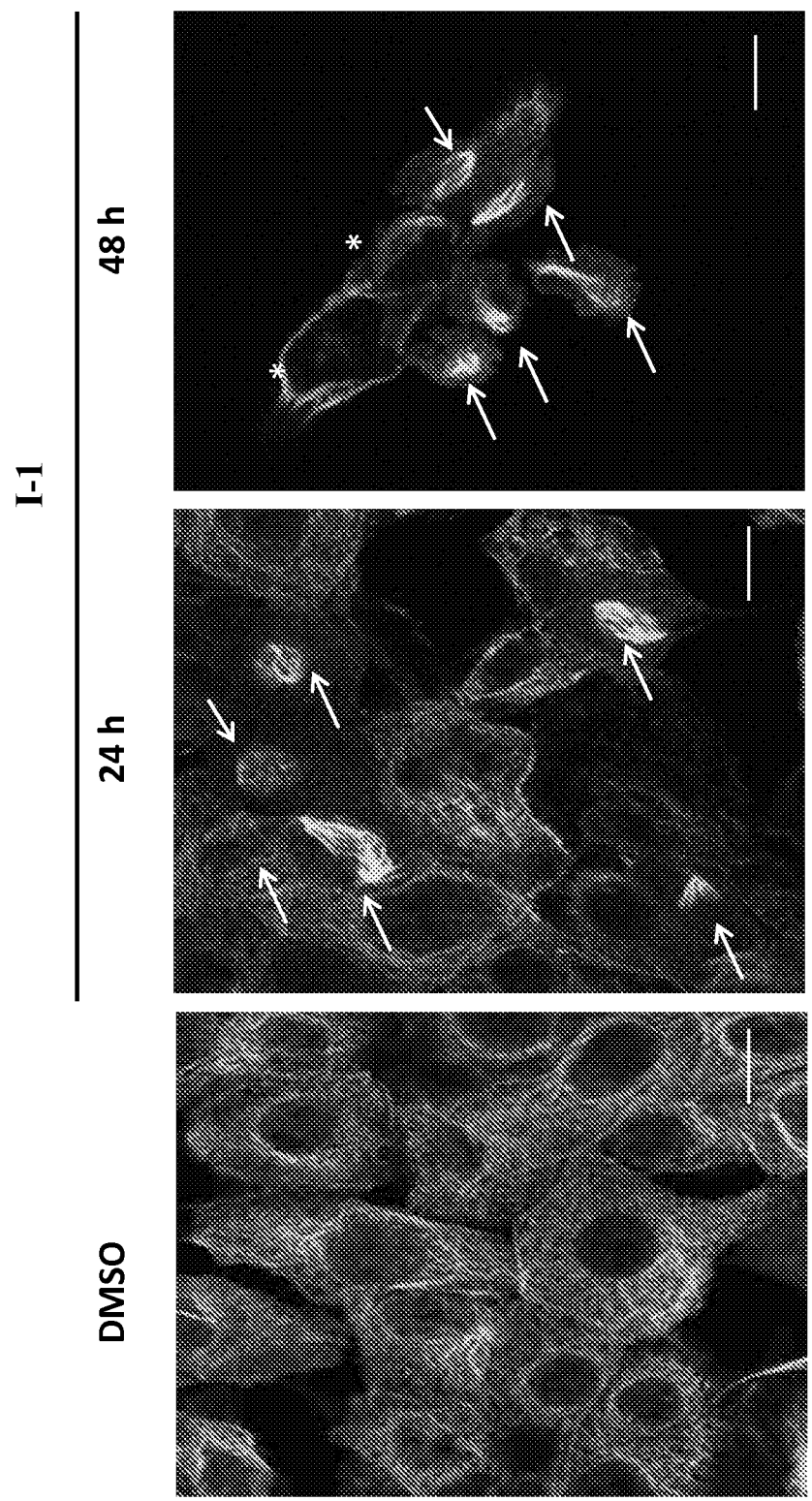
FIG. 14. Fluorescent microscopy of DU145 prostate cancer cells. DU145 cells were plated in culture dishes designed for confocal microscopy and allowed to adhere for 18 hours at 37° C. They were then for incubated for a further 24 and 48 h with 10 μM compound I-1 or 48 h with vehicle (DMSO). After that, cells were washed with cold PBS, fixed with 4% paraformaldehyde, and permeabilized with 0.1% Triton 100X. Cells were stained with 4'6-diamidino-2-phenylindole (DAPI), which binds to DNA, and with anti-α-tubulin antibody labeled with Alexa Fluor 488 to show the location of microtubules. Scale bars indicate a length of 10 nm, arrows indicate cells with evidence of aberrant mitosis, and asterisks indicate cells with apoptotic morphology.

Finally, to verify that our cytometric analyses and biochemical findings correlated with the morphological appearance of cells, we performed confocal microscopy to examine cells that had been fluorescently stained for α-tubulin (to detect microtubules) and DAPI (to detect DNA). The results (FIG. 14) showed that, after 24 h treatment with compound I-1 (10 μM), there was an increased number of DU145 cells that displayed evidence of aberrant mitosis (white arrows). These were characterized by condensed chromosomes and mitotic spindles, but in most case both the chromosomes and microtubules were different to what would be expected for normal mitosis. After 48 h treatment with compound I-1, almost all of the cells show evidence of abnormal mitosis (white arrows) or apoptosis (white asterisks).

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the specification, "a" or "an" may mean one or more. As used in the claims, when used in conjunction with the word "comprising," the words "a" or "an" may mean one or more than one. As used herein "another" may mean at least a second or more. As used in the specification, the phrases "such as" and "e.g." mean "for example, but not limited to" in that the list following "such as" or "e.g." provides some examples but is not necessarily a fully inclusive list.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

The invention claimed is:

1. A composition comprising a compound, wherein the compound is selected from the group consisting of Formula (I), salts of Formula (I), isomers of Formula (I), and derivatives of Formula (I), and the concentration of the compound is at least about 0.20% by weight and Formula (I) is

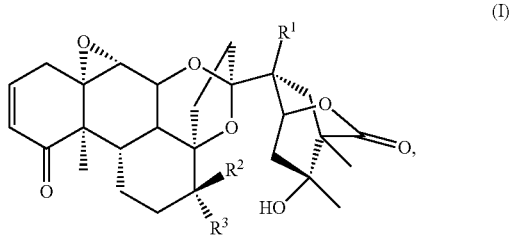

(I)

where $R^1$, $R^2$, and $R^3$ can be the same or different, and are selected from the group consisting of H, halogen, hydroxyl, methoxy, ethoxy, propoxy, butoxy, pentoxy, hexoxy, methyl, ethyl, propyl, butyl, pentyl, hexyl, and heptyl.

2. The composition of claim 1, wherein the concentration of the compound is at least about 10.0% by weight.

3. The composition of claim 1, wherein the concentration of the compound is at least about 50.0% by weight.

4. The composition of claim 1, wherein the concentration of the compound is at least about 90.0% by weight.

5. The composition of claim 1, wherein $R^1$, $R^2$, and $R^3$ can be the same or different and are selected from group consisting of H, hydroxyl, halogen, methyl, ethyl, methoxy, and ethoxy.

6. The composition of claim 1, wherein the compound is selected from the group consisting of I-1, I-2, and I-3.

7. The composition of claim 1, wherein the compound causes arrest in the $G_2/M$ phase of the cell cycle or induces apoptosis.

8. A composition comprising a compound, wherein the composition is a pharmaceutical composition and the compound is selected from the group consisting of Formula (I), salts of Formula (I), isomers of Formula (I), and derivatives of Formula (I), and Formula (I) is

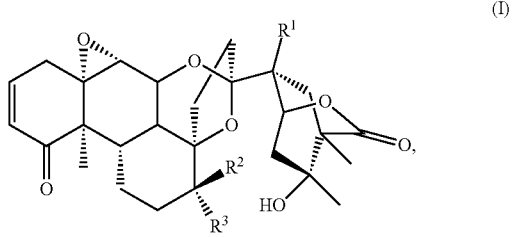

(I)

where $R^1$, $R^2$, and $R^3$ can be the same or different, and are selected from the group consisting of H, halogen, hydroxyl, methoxy, ethoxy, propoxy, butoxy, pentoxy, hexoxy, methyl, ethyl, propyl, butyl, pentyl, hexyl, and heptyl.

9. The composition of claim 8, wherein the concentration of the compound is at least about 10.0% by weight.

10. The composition of claim 8, wherein the compound is selected from the group consisting of I-1, I-2, and I-3.

11. The composition of claim 8, wherein the compound causes arrest in the $G_2/M$ phase of the cell cycle or induces apoptosis.

12. The composition of claim 8, wherein the compound is present in a therapeutically effective amount to treat a disease.

13. The composition of claim 8, wherein the compound is present in a therapeutically effective amount to treat a cancer.

14. The composition of claim 8, wherein the composition further comprises a formulary ingredient or pyrogen-free water.

15. A method for treating a disease in an animal comprising
administering to the animal a composition comprising a compound,
wherein the compound is selected from the group consisting of Formula (I), salts of Formula (I), isomers of Formula (I), and derivatives of Formula (I), and the disease is cancer and Formula (I) is

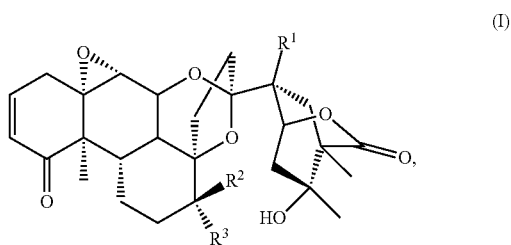

(I)

where $R^1$, $R^2$, and $R^3$ can be the same or different, and are selected from the group consisting of H, halogen, hydroxyl, methoxy, ethoxy, propoxy, butoxy, pentoxy, hexoxy, methyl, ethyl, propyl, butyl, pentyl, hexyl, and heptyl.

16. The method of claim 15, further comprising identifying an animal with the disease.

17. The method of claim 15, wherein the the disease comprises a cancerous tumor.

18. The method of claim 15, wherein the disease is a cancer selected from the group consisting of basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, and leukemias.

19. The method of claim 15, wherein the compound causes arrest in the $G_2/M$ phase of the cell cycle or induces apoptosis.

20. The method of claim 15, wherein the animal is a mammal or a human.

21. The method of claim 15, wherein the administering is by an oral route or by a parenteral route.

22. The method of claim 15, wherein the concentration of the compound is at least about 10.0% by weight.

23. The method of claim 15, wherein the compound is selected from the group consisting of I-1, I-2, and I-3.

24. The method of claim 15, wherein the disease is a cancer selected from the group consisting of breast cancer, colon cancer, lung cancer, ovarian cancer, melanoma, renal cell carcinoma, pancreatic cancer, prostate cancers, chronic lymphocytic leukemia (CLL), acute lymphoblastic leukemia, bladder cancer, gastric cancer, rectal cancer, stomach cancer, uterine cancer, and leukemias.

25. The composition of claim 1, wherein the composition does not consist of I-1, I-2, I-3, or combinations thereof.

26. The composition of claim 8, wherein the composition does not consist of I-1, I-2, I-3, or combinations thereof.

* * * * *